(12) United States Patent
Takii et al.

(10) Patent No.: US 10,980,412 B2
(45) Date of Patent: Apr. 20, 2021

(54) SUBJECTIVE OPTOMETRY APPARATUS AND STORAGE MEDIUM

(71) Applicant: NIDEK CO., LTD., Aichi (JP)

(72) Inventors: Michihiro Takii, Aichi (JP); Hirohisa Terabe, Aichi (JP)

(73) Assignee: NIDEK CO., LTD., Aichi (JP)

( * ) Notice: Subject to any disclaimer, the term of this patent is extended or adjusted under 35 U.S.C. 154(b) by 175 days.

(21) Appl. No.: 16/282,741

(22) Filed: Feb. 22, 2019

(65) Prior Publication Data

US 2019/0269318 A1    Sep. 5, 2019

(30) Foreign Application Priority Data

Mar. 2, 2018  (JP) .............................. JP2018-037629

(51) Int. Cl.
| | |
|---|---|
| A61B 3/02 | (2006.01) |
| A61B 3/028 | (2006.01) |
| A61B 3/036 | (2006.01) |
| A61B 3/103 | (2006.01) |
| A61B 3/18 | (2006.01) |
| A61B 3/032 | (2006.01) |

(52) U.S. Cl.
CPC ............ *A61B 3/0285* (2013.01); *A61B 3/032* (2013.01); *A61B 3/036* (2013.01); *A61B 3/103* (2013.01); *A61B 3/1035* (2013.01); *A61B 3/18* (2013.01)

(58) Field of Classification Search
CPC ....... A61B 3/028; A61B 3/0008; A61B 3/085; A61B 3/08; A61B 3/13; A61B 3/022; A61B 3/063; A61B 3/066; A61B 3/032; A61B 3/0033; A61B 3/036; A61B 3/02

USPC .......................................... 351/237–246, 222
See application file for complete search history.

(56) References Cited

U.S. PATENT DOCUMENTS

| | | | |
|---|---|---|---|
| 5,610,671 A | * | 3/1997 | Hosoi .................... A61B 3/028 351/200 |
| 5,859,688 A | | 1/1999 | Hosoi et al. |
| 2017/0135572 A1 | | 5/2017 | Takii et al. |

FOREIGN PATENT DOCUMENTS

| | | |
|---|---|---|
| EP | 3 381 350 A1 | 10/2018 |
| EP | 3 461 395 A2 | 4/2019 |
| JP | 5-176893 A | 7/1993 |

(Continued)

OTHER PUBLICATIONS

Search Report dated Jul. 8, 2019 by the European Patent Office in counterpart European Patent Application No. 19158216.2.

*Primary Examiner* — Hung X Dang
(74) *Attorney, Agent, or Firm* — Sughrue Mion, PLLC

(57) ABSTRACT

A subjective optometry apparatus includes a light projecting optical system that has a visual target presenting portion for emitting a target light flux and projects a target light flux emitted from the visual target presenting portion toward a subject eye, a calibration portion that is disposed in an optical path of the light projecting optical system and changes optical characteristics of the target light flux, an acquisition portion that acquires a near distance objective eye refractive power that is an eye refractive power of the subject eye objectively measured in a near distance viewing state, and a control portion that controls an operation for acquiring a near distance subjective eye refractive power that is a subjective eye refractive power of the subject eye measured in a near distance viewing state, based on the near distance objective eye refractive power.

9 Claims, 10 Drawing Sheets

(56) References Cited

FOREIGN PATENT DOCUMENTS

JP     2017-86652 A     5/2017

\* cited by examiner

SUBJECTIVE OPTOMETRY APPARATUS AND STORAGE MEDIUM

CROSS-REFERENCE TO RELATED APPLICATION

This application claims priority from Japanese Patent Application No. 2018-037629 filed on Mar. 2, 2018, the entire subject-matter of which is incorporated herein by reference.

TECHNICAL FIELD

The present disclosure relates to a subjective optometry apparatus and a storage medium storing a subjective optometry program for subjectively measuring a subjective eye refractive power of a subject eye.

BACKGROUND

A subjective optometry apparatus for subjectively examining (measuring) an eye refractive power and the like of a subject eye by disposing optical elements, such as a spherical lens or a cylindrical (astigmatic) lens, in an examination window of an optometry unit and by presenting a visual target to the subject eye through the disposed optical elements, using a calibration portion (for example, an optometry unit) disposed in front of the eyes of an examinee, is known (refer to JP-A-H05-176893). Such a subjective optometry apparatus acquires an objective eye refractive power which is objectively measured and performs subjective examination using the acquired objective eye refractive power.

Further, in recent years, there has been an increase in a tendency to use dedicated eyeglasses according to an intended use (for far distance viewing, for near distance viewing, or the like), an increase in a frequency of using multifocal lenses (for example, progressive lens and the like, and in addition to the subjective acquisition of the eye refractive power in a far distance viewing state, opportunities to subjectively acquire the eye refractive power in a near distance viewing state are increasing.

In the related art, the subjective examination was performed using only the objective eye refractive power which is objectively measured in the far distance viewing state. For example, even in a case of measuring a near distance subjective eye refractive power which is the subjective eye refractive power of the subject eye in the near distance viewing state, a far distance objective eye refractive power was used. Therefore, there was a case where the acquisition of the near distance subjective eye refractive power could not be achieved excellently.

SUMMARY

An object of the present disclosure is to provide a subjective optometry apparatus and a storage medium storing a subjective optometry program which can excellently acquire a near distance subjective eye refractive power.

In order to solve the above-described problem, the invention includes the following configurations.

(1) A subjective optometry apparatus for acquiring a subjective eye refractive power by subjectively measuring an eye refractive power of a subject eye, including:

a light projecting optical system that has a visual target presenting portion for emitting a target light flux, and projects a target light flux emitted from the visual target presenting portion toward the subject eye;

a calibration portion that is disposed in an optical path of the light projecting optical system, and changes optical characteristics of the target light flux;

an acquisition portion configured to acquire a near distance objective eye refractive power that is an eye refractive power of the subject eye objectively measured in a near distance viewing state; and a control portion configured control an operation for acquiring a near distance subjective eye refractive power that is a subjective eye refractive power of the subject eye measured in a near distance viewing state, based on the near distance objective eye refractive power.

(2) The subjective optometry apparatus according to the above-described (1), in which the control portion sets the near distance objective eye refractive power as an initial value of the calibration portion when the control portion acquires the near distance subjective eye refractive power.

(3) The subjective optometry apparatus according to the above-described (2), in which the control portion sets at least near distance objective astigmatism information indicating the near distance objective eye refractive power as an initial value in the calibration portion when the control portion acquires the near distance subjective eye refractive power.

(4) The subjective optometry apparatus according to the above-described (1), in which in a case where the control portion acquires the near distance subjective eye refractive power based on a far distance subjective eye refractive power that is a subjective eye refractive power of the subject eye measured in a far distance viewing state, the control portion acquires the far distance subjective eye refractive power, and sets at least any parameter of the far distance subjective eye refractive power to be changeable to a corresponding parameter in the near distance objective eye refractive power based on a comparison result of the near distance objective eye refractive power and the far distance subjective eye refractive power.

(5) The subjective optometry apparatus according to the above-described (4), in which the comparison result is a result of comparing at least far distance subjective astigmatism information of the far distance subjective eye refractive power with at least near distance objective astigmatism information of the near distance objective eye refractive power.

(6) The subjective optometry apparatus according to the above-described (4), in which the control portion acquires a difference information between the near distance objective eye refractive power and the far distance subjective eye refractive power as the comparison result, and sets at least any parameter of the far distance subjective eye refractive power to be changeable to a corresponding parameter in the near distance objective eye refractive power based on the difference information.

(7) The subjective optometry apparatus according to the above-described (1), further including:

a housing that accommodates the light projecting optical system; and a holding member that holds the calibration portion,
in which the holding member integrally connects the housing and the calibration portion.

(8) A non-transitory computer readable recording medium storing a subjective optometry program used in a subjective optometry apparatus for acquiring a subjective eye refractive power by subjectively measuring an eye refractive power of a subject eye, including a light projecting optical system that has a visual target presenting portion for emitting a target light flux and projects a target light flux emitted from the visual target presenting portion toward the subject eye, and a calibration portion that is disposed in an optical path of the light projecting optical system and changes optical characteristics of the target light flux,
in which the subjective optometry program is executed by a processor of the subjective optometry apparatus to cause the subjective optometry apparatus to execute:
a step of acquiring a near distance objective eye refractive power that is an eye refractive power of the subject eye objectively measured in a near distance viewing state; and
a step of controlling an operation for acquiring a near distance subjective eye refractive power that is a subjective eye refractive power of the subject eye measured in a near distance viewing state, based on the near distance objective eye refractive power.

DETAILED DESCRIPTION

<Outline>

Figure 1A:
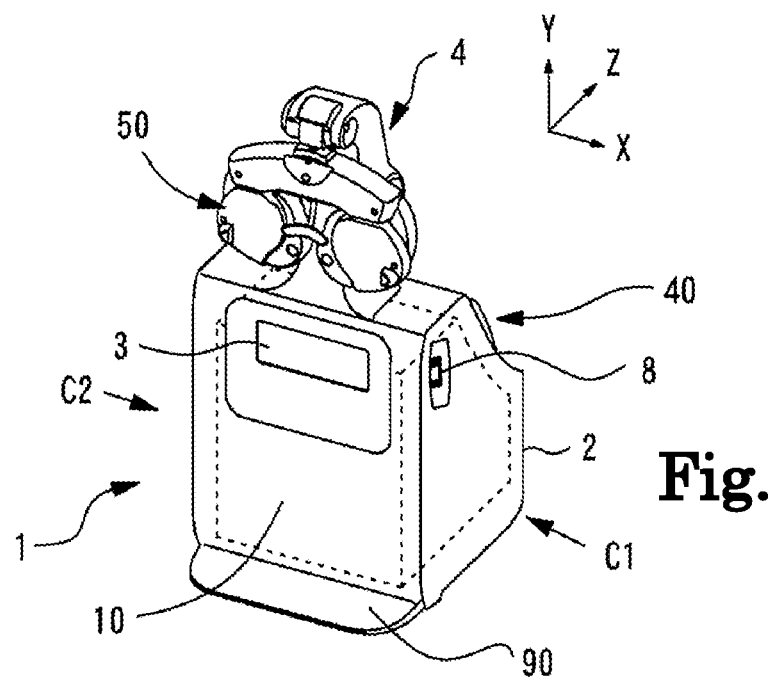
FIGS. 1A and 1B are perspective views illustrating a subjective optometry apparatus from a front side.

Hereinafter, one of typical embodiments will be described with reference to the drawings. FIGS. 1A to 10B are views for describing a subjective optometry apparatus according to the present embodiment. In addition, items classified as the following sign "< >" may be used independently of or in relation to each other.

Further, in the following description, a description will be given on the assumption that a depth direction (a front-rear direction of an examinee when the examinee is measured) of the subjective optometry apparatus is a Z direction, a horizontal direction on a plane which is perpendicular (a left-right direction of the examinee when the examinee is measured) to the depth direction is an X direction, and a vertical direction (an up-down direction of the examinee when the examinee is measured) is a Y direction.

In addition, the present disclosure is not limited to the apparatus described in the present embodiment. For example, terminal control software (program) for performing the function of the following embodiment is supplied to a system or an apparatus through a network, any of various storage mediums, or the like. In addition, a control device (for example, a CPU or the like) of the system or the apparatus can also read out and execute a program.

For example, the subjective optometry apparatus (for example, subjective optometry apparatus 1) of the present embodiment is used for acquiring a subjective eye refractive power by subjectively measuring an eye refractive power of a subject eye. For example, at least any one of spherical surface information (for example, a spherical power (S)), astigmatism information (for example, at least any one of an astigmatic power (C) and an astigmatic axis angle (A)), and the like may be employed as the eye refractive power. In addition, the subjective optometry apparatus of the present embodiment may obtain optical characteristics different from the subjective eye refractive power. For example, the subjectively-measured optical characteristics of the subject eye may be at least any one of contrast sensitivity, binocular visual function (for example, oblique amount, stereoscopic visual function, and the like), and the like.

For example, the subjective optometry apparatus may include a visual target presenting portion (for example, a display 11) that emits a target light flux, and may include a light projecting optical system (for example, a light projecting optical system 10) that projects the target light flux emitted from the visual target presenting portion toward the subject eye. For example, the subjective optometry apparatus may include a housing (for example, a housing 2) that accommodates the light projecting optical system.

For example, the subjective optometry apparatus may include the visual target presenting portion (for example, the display 11) that emits the target light flux, and may include the light projecting optical system (for example, the light projecting optical system 10) that projects the target light flux emitted from the visual target presenting portion toward the subject eye. In addition, for example, the subjective optometry apparatus may include a calibration portion (for example, an optometry unit 50) which is disposed in an optical path of the light projecting optical system and changes the optical characteristics of the target light flux.

For example, the subjective optometry apparatus may include an acquisition portion (for example, a control portion 80) for acquiring a near distance objective eye refractive power obtained by objectively measuring an eye refractive power of the subject eye in a near distance viewing state. Further, for example, the subjective optometry apparatus may include a control portion (for example, the control portion 80) for controlling an operation when acquiring the near distance subjective eye refractive power which is the subjective eye refractive power of the subject eye in the near distance viewing state based on the near distance objective eye refractive power.

For example, it is ascertained that there is a difference in measurement results between the near distance objective eye refractive power which is objectively measured in the near distance viewing state and the far distance objective eye refractive power measured in the far distance viewing state. Therefore, as described above, for example, based on the near distance objective eye refractive power, the operation when acquiring the near distance subjective eye refractive power which is the subjective eye refractive power of the subject eye is controlled, and accordingly, it is possible to perform the subjective examination in the near distance viewing state taking into account the near distance objective eye refractive power. Accordingly, it is possible to excellently acquire the near distance subjective eye refractive power.

For example, the near distance viewing state indicates a state where a presentation distance of the visual target is presented in the near presentation distance (near distance) for the subject eye. For example, by performing the measurement in a state where the visual target is presented in the near presentation distance, it is possible to acquire the measurement result (for example, the near distance subjective eye refractive power in the near distance viewing state, the near distance objective eye refractive power in the near distance viewing state, and the like) in the near distance viewing state. In addition, the near distance viewing state may include an intermediate distance viewing state. For example, the intermediate distance viewing state indicates a state where a presentation distance of the visual target is presented in the intermediate presentation distance (intermediate distance).

For example, the near distance objective eye refractive power may be indicated with at least any one of the spherical surface information (for example, a spherical power), astigmatism information, and the like of the subject eye in the near distance viewing state. For example, the astigmatism information may be at least any one of the astigmatic power (cylindrical surface power) and the astigmatic axis angle (axis angle).

<Light Projecting Optical System>

For example, a configuration may also be employed in which a display is used as the visual target presenting portion. For example, the display may be at least any one of a liquid crystal display (LCD), a liquid crystal on silicon (LCOS), an organic electro luminescence (EL), and the like. For example, an examination visual target, such as a Landolt ring visual target, is displayed on the display.

In addition, for example, a digital micromirror device (DMD) may be used as the visual target presenting portion. In general, the DMD has high reflectivity and luminance. Therefore, it is possible to maintain the amount of light of the target light flux compared to a liquid crystal display even in a case where polarization is used.

In addition, for example, as the visual target presenting portion, a configuration including a visual target presenting visible light source and a visual target plate may be employed. In this case, for example, the visual target plate is a rotatable disk plate, and includes a plurality of visual targets. The plurality of visual targets include, for example, a visual target for examination of visual acuity which is used during the subjective measurement, and the like. For example, regarding the visual target for examination of visual acuity, a visual target (visual acuity value 0.1, 0.3, . . . , 1.5) is provided for each visual acuity value. For example, the visual target plate is rotated by a motor or the like, and the visual targets are disposed in a switching manner on the optical path through which the target light flux is guided to the subject eye. It is needless to say that a visual target presenting portion other than the above-described configuration may be used as the visual target presenting portion that projects the target light flux.

For example, the light projecting optical system may include at least one or more optical members that project the target light flux toward the subject eye. For example, the light projecting optical system may include an optical member (for example, a concave surface mirror 13) which optically guides an image of the target light flux emitted from the visual target presenting portion to the subject eye so as to have a predetermined examination distance.

For example, in the light projecting optical system, the target light flux emitted from the visual target presenting portion is shifted with respect to an optical axis of the optical member so as to be incident thereon, and the target light flux is projected toward the subject eye. In this case, for example, the visual target presenting portion may be disposed by tilting a normal direction to an image surface of the visual target presenting portion with respect to the optical axis of the optical member.

For example, the optical member may be at least one of a concave surface mirror, a lens, and the like. For example, in a case where the optical member is a concave surface mirror, the light projecting optical system may include a reflection member (for example, a flat surface mirror 12) which reflects the target light flux emitted by the visual target presenting portion toward the concave surface mirror and guides the target light flux reflected by the concave surface mirror from the inside to the outside of the housing. With such a configuration, it is possible to reduce the number of members of the light projecting optical system and to save the space of the subjective optometry apparatus. It is needless to say that the light projecting optical system is not limited to the above-described configuration, and a configuration in which the target light flux emitted from the visual target presenting portion is shifted with respect to the optical axis of the optical member so as to be incident thereon and the target light flux is projected toward the subject eye may be employed.

For example, the reflection member may be any one of a mirror (for example, a total reflection mirror, a half mirror, and the like), a prism, and the like. It is needless to say that the reflection member is not limited thereto, and a member which guides the target light flux toward the subject eye may be employed.

For example, in the present embodiment, the light projecting optical system may include a right eye light projecting optical system and a left eye light projecting optical system which are provided as a pair on the left and right sides respectively. In this case, for example, a visual target presenting portion provided as a pair on the left and right sides may be used. For example, the right eye light projecting optical system and the left eye light projecting optical system may be configured such that members configuring the right eye light projecting optical system and members configuring the left eye light projecting optical system are configured with the same member. In addition, for example, the right eye light projecting optical system and the left eye light projecting optical system may be configured such that at least some of the members configuring the right eye light projecting optical system and the members configuring the left eye light projecting optical system are configured with different members. For example, the right eye light projecting optical system and the left eye light projecting optical system may be configured such that at least some of the members configuring the right eye light projecting optical system and the members configuring the left eye light projecting optical system are used in common. In addition, for example, the right eye light projecting optical system and the left eye light projecting optical system may be configured such that the members configuring the right eye light projecting optical system and the members configuring the left eye light projecting optical system are separately provided.

<Calibration Portion>

For example, the calibration portion may be configured to change the optical characteristics (for example, at least any one of the spherical power, the cylindrical surface power (astigmatic power), the astigmatic axis angle, the polarization characteristics, and the amount of aberration) of the target light flux. For example, as a configuration in which the optical characteristics of the target light flux is changed, a configuration in which an optical element is controlled may be employed. For example, as the optical element, a configuration may also be employed in which at least any one of a spherical lens, a cylindrical lens, a cross cylinder lens, a rotary prism, a wavefront modulation element, and the like is used. It is needless to say that, for example, as the optical element, an optical element different from the optical element having the above-described configuration may be used.

For example, the calibration portion may be configured such that the spherical power of the subject eye is calibrated as a presentation position (presentation distance) of the visual target with respect to the eyes of the examinee is optically changed. In this case, for example, as a configuration in which the presentation position (presentation distance) of the visual target is optically changed, a configuration may also be employed in which a light source (for example, a display) is moved in a direction of the optical axis. In addition, in this case, for example, a configuration may also be employed in which the optical element (for example, a spherical lens) which is disposed in the optical path is moved in the direction of the optical axis. It is needless to say that the calibration portion may have a configuration combined by a configuration in which the optical element is controlled and a configuration in which the optical element disposed in the optical path is moved in the direction of the optical axis.

For example, the calibration portion may be an optometry unit (phoropter) in which optical elements disposed in front of the subject eye are disposed in a switching manner. For example, the optometry unit may be configured to include a pair of left and right lens chamber units for switching and disposing the optical elements in the examination window. For example, the optometry unit may be configured to include a lens disk having a plurality of optical elements disposed on the same circumference thereof and a driving portion for rotating the lens disk, and to electrically switch the optical elements by the driving of the driving portion (for example, a motor).

For example, the calibration portion may be configured to change the optical characteristics of the target light flux by disposing the optical element between the optical member for guiding the target light flux toward the subject eye from the light projecting optical system and the light source of the light projecting optical system and by controlling the optical element. In other words, the calibration portion may have a configuration of a phantom lens refractometer (phantom calibration means). In this case, for example, the target light flux calibrated by the calibration portion is guided to the subject eye through the optical members.

For example, in the present embodiment, the calibration portion includes a right eye calibration portion and a left eye calibration portion which are provided as a pair on the left and right sides, respectively. For example, the right eye calibration portion and the left eye calibration portion may be configured such that members configuring the right eye calibration portion and members configuring the left eye calibration portion are configured with the same member. In addition, for example, the right eye calibration portion and the left eye calibration portion may be configured such that at least some of the members configuring the right eye calibration portion and the members configuring the left eye calibration portion are configured with different members. For example, the right eye calibration portion and the left eye calibration portion may be configured such that at least some of the members configuring the right eye calibration portion and the members configuring the left eye calibration portion are used in common. In addition, for example, the right eye calibration portion and the left eye calibration portion may be configured such that the members configuring the right eye calibration portion and the members configuring the left eye calibration portion are separately provided.

<Acquisition Portion>

For example, the acquisition portion may be configured to acquire the near distance objective eye refractive power by receiving the near distance objective eye refractive power input to the subjective optometry apparatus as the examiner operates the operation portion. In addition, for example, the acquisition portion may be configured to acquire the near distance objective eye refractive power by receiving the near distance objective eye refractive power measured by an apparatus (for example, an objective optometry apparatus) different from the subjective optometry apparatus. In addition, for example, the subjective optometry apparatus may be configured to include an objective measurement portion for measuring the near distance objective eye refractive power, and to acquire the near distance objective eye refractive power by measuring the near distance objective eye refractive power of the subject eye by the objective measurement portion.

<Control Portion>

For example, an example of a configuration for controlling the operation when the control portion acquires the near distance subjective eye refractive power will be described below.

For example, as a configuration for controlling the operation when acquiring the near distance subjective eye refractive power, a configuration for performing the setting the initial value may be employed. For example, the control portion may set the near distance objective eye refractive power as the initial value of the calibration portion when acquiring the near distance subjective eye refractive power. According to this, for example, it is possible to perform the subjective examination in the near distance viewing state with the near distance objective eye refractive power as the initial value. Therefore, it becomes possible to start the subjective examination of the near distance viewing state from the result of the near distance objective eye refractive power, and it becomes possible to rapidly acquire the near distance eye refractive power. In addition, since it is possible to acquire the near distance subjective eye refractive power with the near distance objective eye refractive power as the initial value, it is possible to acquire the near distance subjective eye refractive power with higher accuracy.

For example, the near distance objective eye refractive power set as the initial value may include at least near distance objective astigmatism information. In this case, for example, the control portion may set at least the near distance objective astigmatism information which is the near distance objective eye refractive power as the initial value in the calibration portion when acquiring the subjective eye refractive power. For example, the near distance objective astigmatism information may include at least any one of a near distance objective astigmatic power and a near distance object astigmatic axis.

For example, it is ascertained that there is a difference in measurement results between the near distance objective eye refractive power which is objectively measured in the near distance viewing state and the far distance objective eye refractive power measured in the far distance viewing state, particularly in the astigmatism information. Therefore, for example, as described above, by controlling the operation of the subjective optometry apparatus in consideration of the near distance objective astigmatism information, more appropriate operation can be performed.

In addition, for example, the near distance objective eye refractive power set as the initial value may be different from the configuration including at least the near distance objective astigmatism information. For example, the near distance objective eye refractive power set as the initial value may include at least any one of the near distance objective spherical surface information and the near distance objective astigmatism information.

For example, as the configuration for controlling the operation when acquiring the near distance subjective eye refractive power, a configuration that can change the parameters of the near distance objective eye refractive power and the far distance subjective eye refractive power may be employed. For example, the control portion may acquire the far distance subjective eye refractive power which is the subjective eye refractive power of the subject eye in a far distance viewing state, may set at least any parameter of the far distance subjective eye refractive power to be changeable to a corresponding parameter in the near distance objective eye refractive power based on a comparison result of the near distance objective eye refractive power and the far distance subjective eye refractive power, and may acquire the near distance subjective eye refractive power based on the far distance subjective eye refractive power. With such a configuration, for example, in a case of acquiring the near distance subjective eye refractive power by using the far distance subjective eye refractive power, by making it possible to take into account the near distance viewing state, it is possible to acquire the near distance subjective eye refractive power with higher accuracy. For example, in a case where there is a difference in the eye refractive power between the far distance viewing state and the near distance viewing state, in order to acquire the near distance subjective eye refractive power with higher accuracy, it is preferable to acquire the near distance subjective eye refractive power by taking into account the near distance viewing state. Therefore, for example, by changing the far distance subjective eye refractive power in accordance with the comparison result, it is possible to acquire the near distance subjective eye refractive power that has taken into account the near distance viewing state together with the far distance viewing state, and to acquire an excellent subjective eye refractive power.

For example, the far distance viewing state indicates a state where the presentation distance of the visual target is presented in the far presentation distance (far distance) for the subject eye. For example, by performing the measurements in a state where the visual target is presented in the far presentation distance, it is possible to acquire the measurement result (for example, the far distance subjective eye refractive power in the far distance viewing state, the far distance objective eye refractive power in the far distance viewing state, and the like) in the far distance viewing state.

For example, the far distance subjective eye refractive power may be indicated with at least any one of the spherical surface information (for example, spherical power), astigmatism information, and the like of the subject eye in the far distance viewing state. For example, the astigmatism information may indicate at least any one of the astigmatic power and the astigmatic axis angle.

In addition, for example, based on the comparison result, as a configuration in which at least any parameter of the far distance subjective eye refractive power can be changed to a corresponding parameter in the near distance objective eye refractive power, a configuration in which it is determined whether or not the comparison result exceeds a threshold value set in advance and the change of the parameter is controlled based on the determination result may be employed. For example, a determination portion (for example, the control portion 80) for determining whether or not the comparison result exceeds the threshold value set in advance may be provided. In this case, for example, in a case where the comparison result exceeds the threshold value, at least any parameter of the far distance subjective eye refractive power may be changed to a corresponding parameter in the near distance objective eye refractive power and the near distance subjective eye refractive power may be acquired. In addition, in this case, for example, in a case where the comparison result does not exceed the threshold value, at least any parameter of the far distance subjective eye refractive power may not be changed to a corresponding parameter in the near distance objective eye refractive power and the near distance subjective eye refractive power may be acquired. In addition, for example, as the threshold value, a threshold value for determining that it is necessary to change the parameter by simulation, experiment or the like may be set in advance. For example, a configuration may also be employed in which the threshold value can be set to any value by the examiner.

In addition, for example, based on the comparison result, as a configuration in which at least any parameter of the far distance subjective eye refractive power can be changed to a corresponding parameter in the near distance objective eye refractive power, a configuration may be employed in which the change of the parameter is controlled based on whether or not there is a difference between at least any parameter of the far distance subjective eye refractive power and the corresponding parameter in the near distance objective eye refractive power.

For example, the comparison result may be a result of comparing at least the far distance subjective astigmatism information of the far distance subjective eye refractive power with at least the near distance objective astigmatism information of the near distance objective eye refractive power. For example, it is ascertained that there is a difference in measurement results between the near distance objective eye refractive power which is objectively measured in the near distance viewing state and the far distance subjective eye refractive power measured in the far distance viewing state, particularly in the astigmatism information. Therefore, for example, in a case of using the far distance subjective eye refractive power as the near distance subjective eye refractive power, it is easy to confirm whether or not the near distance viewing state is supposed to be considered by comparing the astigmatism information. Therefore, by comparing the astigmatism information, it is possible to easily confirm whether or not the near distance objective eye refractive power is acquired by taking into account the near distance viewing state with respect to the far distance subjective eye refractive power, and to more easily acquire the near distance subjective eye refractive power with higher accuracy.

In addition, for example, the comparison result may be a result different from the result of the comparison between the far distance subjective astigmatism information in the far distance subjective eye refractive power and the near distance objective astigmatism information in the near distance objective eye refractive power. For example, the comparison result may be a result obtained by comparing far distance subjective spherical surface information of the far distance subjective eye refractive power with near distance objective spherical surface information in the near distance objective eye refractive power.

For example, the comparison result may be acquired by the control portion. In this case, for example, the control portion may acquire the comparison result by comparing the near distance objective eye refractive power with the far distance subjective eye refractive power. In addition, for example, the comparison result may be acquired by a part different from the control portion.

For example, the comparison result is acquired by the comparison between the corresponding parameters in the far distance subjective eye refractive power and the near distance objective astigmatism information. As an example, for example, the far distance subjective astigmatism information of the far distance subjective eye refractive power may be compared with the near distance objective astigmatism information in the near distance objective eye refractive power. In this case, for example, the far distance subjective astigmatic power of the far distance subjective eye refractive power may be compared with the near distance objective astigmatic power in the near distance objective eye refractive power. In addition, as an example, for example, the far distance subjective astigmatic axis angle of the far distance subjective eye refractive power may be compared with the near distance objective astigmatic axis angle in the near distance objective eye refractive power.

For example, the comparison result may be information that can compare the near distance objective eye refractive power with the far distance subjective eye refractive power. For example, the comparison result may be ratio information between the near distance objective eye refractive power with the far distance subjective eye refractive power. In addition, for example, the comparison result may be information acquired by differentiating the near distance objective eye refractive power and the far distance subjective eye refractive power. In this case, for example, the control portion may acquire difference information (for example, a difference value between the parameters) between the near distance objective eye refractive power and the far distance subjective eye refractive power as the comparison result, and may be capable of changing at least any parameter of the far distance subjective eye refractive power to a corresponding parameter in the near distance objective eye refractive power based on the difference information.

In addition, for example, based on the difference information, as a configuration in which at least any parameter of the far distance subjective eye refractive power can be changed to a corresponding parameter in the near distance objective eye refractive power, a configuration in which it is determined whether or not the difference information exceeds a threshold value set in advance and the change of the parameter is controlled based on the determination result may be employed. For example, the determination portion (for example, the control portion 80) for determining whether or not the difference information exceeds the threshold value set in advance may be provided. In this case, for example, in a case where the difference information exceeds the threshold value, at least any parameter of the far distance subjective eye refractive power may be changed to a corresponding parameter in the near distance objective eye refractive power and the near distance subjective eye refractive power may be acquired. In addition, in this case, for example, in a case where the difference information does not exceed the threshold value, at least any parameter of the far distance subjective eye refractive power may not be changed to a corresponding parameter in the near distance objective eye refractive power and the near distance subjective eye refractive power may be acquired.

In addition, for example, as the threshold value, a threshold value for determining that it is necessary to change the parameter by simulation, experiment or the like may be set in advance. For example, a configuration may also be employed in which the threshold value can be set to any value by the examiner.

For example, as the configuration for controlling the operation when acquiring the near distance objective eye refractive power, a configuration for adding the difference information to the far distance subjective eye refractive power based on the difference information (for example, a difference value) between the near distance subjective eye refractive power and the far distance objective eye refractive power. In this case, for example, the control portion may acquire the difference information between the near distance objective eye refractive power and the far distance objective eye refractive power, and may add the acquired difference information to the far distance subjective eye refractive power. With such a configuration, for example, in a case of acquiring the near distance subjective eye refractive power by using the far distance subjective eye refractive power, it is possible to acquire the near distance subjective eye refractive power with higher accuracy.

For example, the difference information between the near distance objective eye refractive power and the far distance objective eye refractive power may be acquired by the control portion. In this case, for example, the control portion may acquire the difference information between the near distance objective eye refractive power and the far distance objective eye refractive power. In addition, for example, the difference information between the near distance objective eye refractive power and the far distance objective eye refractive power may be acquired by a part different from the control portion.

For example, the difference information between the near distance objective eye refractive power and the far distance objective eye refractive power may be the result of comparison between at least the far distance objective astigmatism information of the far distance objective eye refractive power and at least the near distance objective astigmatism information of the near distance objective eye refractive power. In addition, for example, the difference information between the near distance objective eye refractive power and the far distance objective eye refractive power may be a result different from the result of comparison between the far distance subjective astigmatism information of the far distance subjective eye refractive power and the near distance objective astigmatism information in the near distance objective eye refractive power. For example, the comparison result may be a result obtained by comparing far distance objective spherical surface information of the far distance objective eye refractive power with near distance objective spherical surface information in the near distance objective eye refractive power.

In addition, in the present embodiment, the acquisition portion, the control portion, and the determination portion may be used in common. In addition, for example, a configuration may also be employed in which the acquisition portion, the control portion, and the determination portion are separately provided. It is needless to say that each of the above-described control portion may be configured with a plurality of control portions.

<Housing and Holding Member>

For example, the subjective optometry apparatus may include a housing (for example, a housing 2) that accommodates the light projecting optical system. For example, the subjective optometry apparatus may include a holding member (for example, a holding arm 35) for holding the calibration portion. For example, in the subjective optometry apparatus, the housing and the calibration portion may be integrally connected to each other. As an example, for example, the holding member may have a configuration in which the housing and the calibration portion are integrally connected to each other.

In addition, for example, in a case where the calibration portion is the optometry unit (for example, the optometry unit 50), for example, in the examination position, the examination window (for example, an examination window 53) of the optometry unit and the presentation window (for example, the presentation window 3) of the housing may be disposed so as to oppose each other.

For example, in the subjective optometry apparatus, the housing and the calibration portion may be integrally connected to each other, or may be configured to be close to each other. For example, the closely disposed configuration may have a distance between the optometry unit and the housing by which the head of the examiner cannot enter. For example, the closely disposed configuration may have a distance between the optometry unit and the housing which is equal to or less than 1 m (for example, 1 m, 500 mm, 135 mm, 70 mm, and the like). It is needless to say, for example, the closely disposed configuration may be a configuration in which the distance between the optometry unit and the housing is greater than 1 m.

Example

Figure 1B:
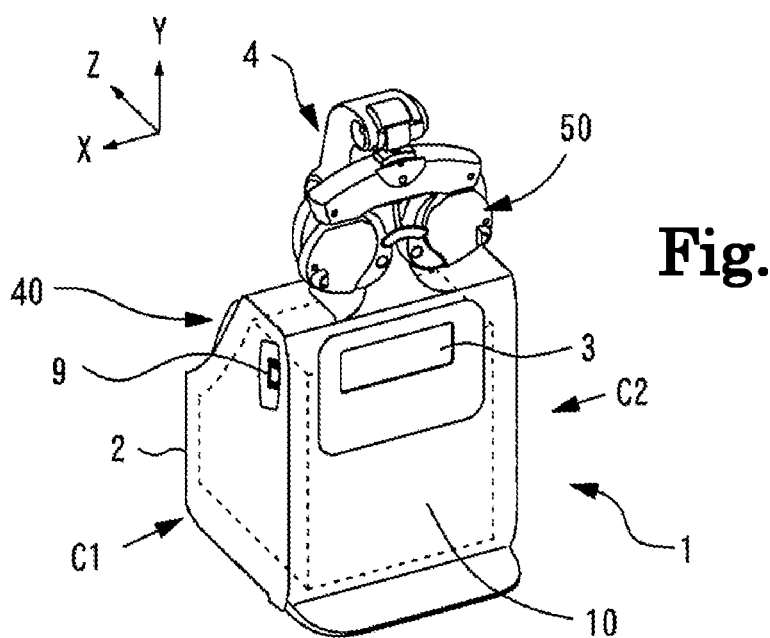
Figure 2:
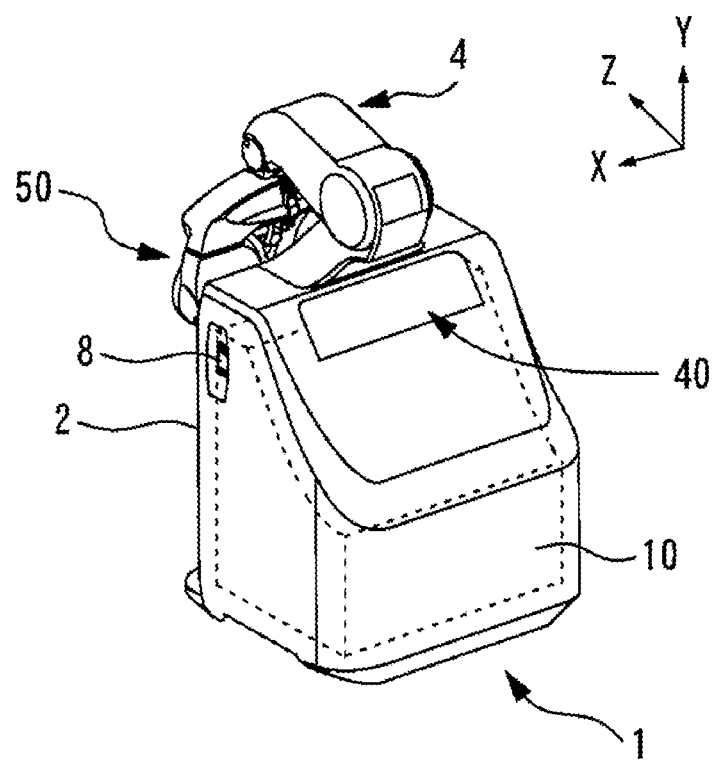
FIG. 2 is a perspective view illustrating a subjective optometry apparatus from a rear side.

Hereinafter, the configuration of the subjective optometry apparatus in the present example will be described. For example, FIGS. 1A and 1B are perspective views illustrating the subjective optometry apparatus 1 from a front side. For example, FIG. 2 is a perspective view illustrating the subjective optometry apparatus 1 according to the present example from a rear side. In addition, in the present example, the side on which the presentation window 3 which will be described later is positioned will be described as the front surface of the subjective optometry apparatus 1, and the side on which an observation window 41 which will be described later is positioned will be described as the rear surface of the subjective optometry apparatus 1. For example, FIG. 1A is a perspective view illustrating the subjective optometry apparatus 1 from the left side of the front surface. In addition, for example, FIG. 1B is a perspective view illustrating the subjective optometry apparatus 1 from the right side of the front surface.

For example, the subjective optometry apparatus 1 includes the housing 2, the presentation window 3, a holding unit 4, a first operation portion 8, a second operation portion 9, the light projecting optical system 10, an observation unit 40, the optometry unit 50, and the like. For example, in the present example, the examinee opposes the front surface of the housing 2. For example, the housing 2 accommodates the light projecting optical system 10 therein. For example, the presentation window 3 is used for presenting the examination visual target to the eyes of the examinee (hereinafter, referred to as a subject eye). For example, the presentation window 3 transmits the target light flux in the light projecting optical system 10. Therefore, the target light flux via the presentation window 3 is projected onto the subject eye. For example, the presentation window 3 is closed with a transparent panel in order to prevent invasion of dust or the like. For example, as a transparent panel, a transparent member, such as an acrylic resin or a glass plate, can be used.

In addition, in a case where the optometry unit 50 is disposed between the presentation window 3 and the subject eye, the target light flux via the presentation window 3 and the examination window 53 of the optometry unit 50 is projected onto the subject eye.

Figure 9:
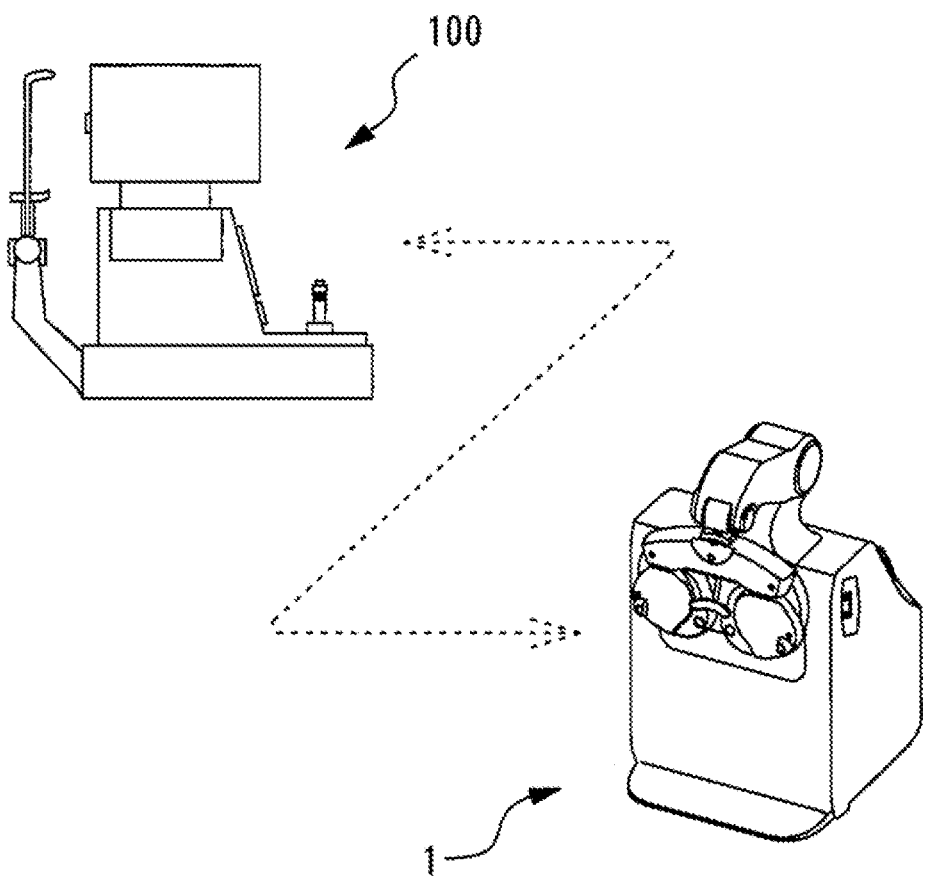
FIG. 9 is a view for describing setting of an initial value.

For example, the holding unit 4 holds the optometry unit 50. For example, by the holding unit 4, the optometry unit 50 is supported in the retreat position or in the examination position. For example, in the retreat position in the present example, as illustrated in FIGS. 1A and 1B, the optometry unit 50 is in a state of being raised above the housing 2. In addition, in the examination position in the present example, as illustrated in FIG. 9, the optometry unit 50 is in a state of being lowered in front of the housing 2. Such switching between the retreat position and the examination position is performed by vertically moving the holding arm 35 (refer to FIGS. 3A and 3B) of the holding unit 4 by a moving unit 6 (refer to FIGS. 3A and 3B) included in the holding unit 4. In addition, in the present example, the holding unit 4 in which the holding arm 35 and the moving unit 6 are integrally configured is provided. It is needless to say that the holding arm 35 and the moving unit 6 may be separately and independently provided.

<Holding Unit>

Figure 3A:
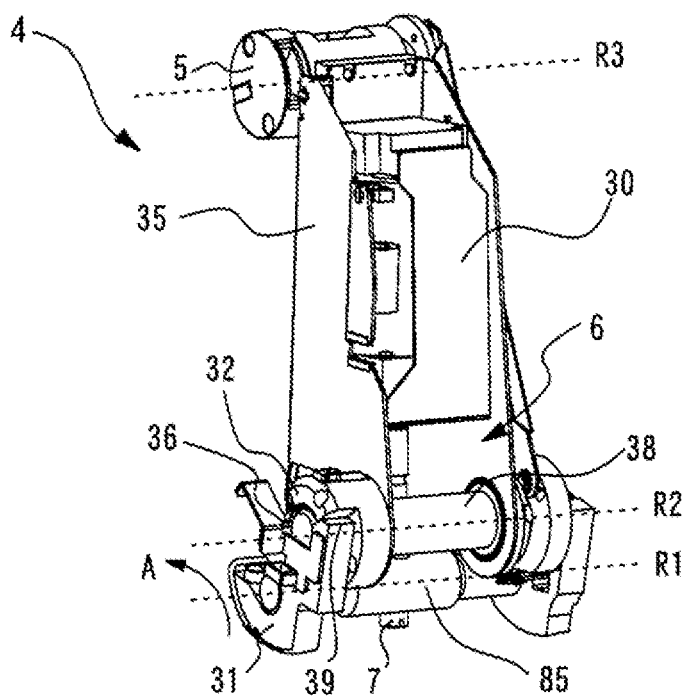
FIGS. 3A and 3B illustrate schematic views of an internal configuration in a case where an external cover of a holding unit is removed.
Figure 3B:
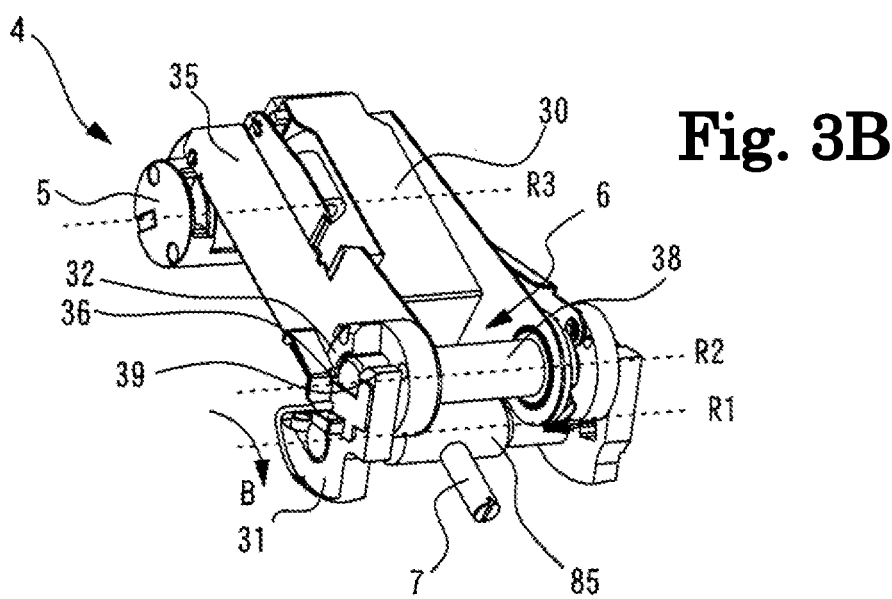

Hereinafter, the holding unit 4 will be described in detail. For example, FIGS. 3A and 3B illustrate schematic views of an internal configuration in a case where an external cover of the holding unit 4 is removed. In addition, in FIGS. 3A and 3B, the optometry unit 50 connected to the holding arm 35 is omitted. For example, FIG. 3A illustrates the internal configuration of the holding unit 4 in a case where the optometry unit 50 is moved to the retreat position. For example, FIG. 3B illustrates the internal configuration of the holding unit 4 in a case where the optometry unit 50 is moved to the examination position.

For example, the holding unit 4 includes a connecting portion 5, the moving unit 6, a base 31, the holding arm 35, and the like. For example, the holding unit 4 is connected to the optometry unit 50 via the connecting portion 5. For example, the connecting portion 5 is rotatably connected to the holding arm 35 around a rotary axis R3. For example, the holding arm 35 is rotatably attached to the base 31. For example, the base 31 is provided on the upper surface of the housing 2. For example, the base 31 is connected to the housing 2 via a connecting portion 33. For example, the base 31 is disposed to be fixed to the housing 2 via the connecting portion 33. In addition, in the present example, a configuration in which the base 31 and the connecting portion 33 are provided separately has been described as an example, but the invention is not limited thereto. The base 31 and the connecting portion 33 may be integrally configured. In this case, for example, the base 31 and the housing 2 may be connected to each other.

For example, the moving unit 6 includes a driving portion (for example, a motor) 30, a shaft 7, a supporting member 85, a block 32, a block receiver 36, a supporting member 38, a block receiver 39, a detector 70, a light shielding portion 71, a slot 72, a restriction member 75, a slot 76, a bearing 77, and the like. In addition, the moving unit 6 may be configured to include at least the motor 30. For example, the motor 30 is fixed to the holding arm 35 and is connected to the upper part of the shaft 7. For example, the lower part of the shaft 7 has a screw portion (not illustrated) and is fitted to the supporting member 85. In other words, the supporting member 85 has a screw portion (not illustrated) at the part through which the shaft 7 penetrates so as to be fitted to the shaft 7. For example, the supporting member 85 is attached to the base 31. For example, the supporting member 85 rotatably supports the shaft 7 with respect to the base 31 around a rotary axis (center axis) R1 of the supporting member 85. For example, the holding arm 35 is attached to the base 31 by the supporting member 38. For example, the supporting member 38 rotatably supports the holding arm 35 with respect to the base 31 around a rotary axis (center axis) R2 of the supporting member 38.

For example, the block 32 is connected to the supporting member 38. For example, the block 32 is rotatable with respect to the base 31 around the rotary axis R2 of the supporting member 38 together with the rotation of the supporting member 38. For example, the block receiver 36 and the block receiver 39 are fixed to the base 31. For example, the block receiver 36 and the block receiver 39 are respectively in contact with the block 32 at different predetermined positions. For example, in a case where the block 32 rotates with respect to the base 31 around the rotary axis R2 of the supporting member 38 in accordance with the rotation of the supporting member 38, when the block 32 rotates to a predetermined position, the block 32 comes into contact with the block receiver 36 or the block receiver 39 provided in the base 31, and the rotation of the block 32 is stopped. For example, in the present example, in the block receiver 36, in a case where the optometry unit 50 reaches the examination position from the retreat position, the block receiver 36 and the block 32 come into contact with each other, and the block receiver 36 is disposed at a position at which the rotation of the block 32 is stopped. In addition, for example, in the present example, in the block receiver 39, in a case where the optometry unit 50 reaches the retreat position from the examination position, the block receiver 39 and the block 32 come into contact with each other, and the block receiver 39 is disposed at a position at which the rotation of the block 32 is stopped.

For example, the operation in which a state where the optometry unit 50 is disposed in the retreat position as illustrated in FIG. 3A becomes a state where the optometry unit 50 is disposed in the examination position as illustrated in FIG. 3B will be described. For example, as the motor 30 is driven, the shaft 7 rotates. For example, as the motor 30 positively rotates, the shaft 7 rotates. As the shaft 7 rotates, the screw portion of the shaft 7 rotates and moves with respect to the supporting member 85 screwed with the screw portion of the shaft 7. In other words, with respect to the supporting member 85, the shaft 7 moves in a shaft direction of the shaft 7. For example, the shaft 7 moves with respect to the supporting member 85 and the part protruding from the supporting member 85 in the shaft 7 increases (the shaft 7 becomes longer). For example, in conjunction with the movement in which the protruding part of the shaft 7 increases, the supporting member 85 rotates in a direction of an arrow A around the rotary axis R1.

For example, as the supporting member 85 rotates around the rotary axis R1, the shaft 7 also rotates around the rotary axis R1. In other words, the shaft 7 moves in the shaft direction of the shaft 7 with respect to the supporting member 85 and rotates in the direction of the arrow A around the rotary axis R1. For example, as the shaft 7 rotates, the motor 30 connected to the shaft 7 rotates in the direction of the arrow A around the rotary axis R1. Further, for example, the holding arm 35 to which the motor 30 is fixed rotates integrally with the rotation of the motor 30 in the direction of the arrow A around the rotary axis R2 of the supporting member 38. Accordingly, the connecting portion 5 connected to the holding arm 35 rotates in the direction of the arrow A, and the optometry unit 50 connected to the connecting portion 5 rotates in the direction of the arrow A. Further, for example, the connecting portion 5 rotates with respect to the holding arm 35 such that the optometry unit 50 can maintain a vertical state by the own weight of the optometry unit 50. In addition, in the present example, the vertical state includes a substantially vertical state. Accordingly, for example, the optometry unit 50 moves from the retreat position as illustrated in FIG. 3A to the examination position as illustrated in FIG. 3B. In other words, the optometry unit 50 can be moved downward.

Further, for example, the rotation (movement to the examination position) of the optometry unit 50 in an A direction is stopped when the optometry unit 50 reaches the examination position by the block 32 and the block receiver 36. For example, with the driving of the motor 30, the block 32 is rotated in the A direction around the rotary axis R2 and comes into contact with the block receiver 36 when the optometry unit 50 reaches the examination position. For example, as the block 32 comes into contact with the block receiver 36, the rotation is stopped. For example, as the block 32 is stopped, the rotation of the supporting member 38 connected to the block 32 is stopped. In addition, according to this, the rotation of the shaft 7 and the supporting member 85 is also stopped. According to this, the optometry unit 50 is stopped in the examination position. In other words, the optometry unit 50 is stopped in the examination position by the block 32 and the block receiver 36.

For example, after the rotation (movement to the examination position) of the optometry unit 50 in the A direction is stopped when the optometry unit 50 reaches the examination position by the block 32 and the block receiver 36, the motor 30 continues to be driven. For example, as the motor 30 is driven, the shaft 7 rotates, but the shaft 7 cannot be moved by the block 32 and the block receiver 36. At this time, for example, the movement of the shaft 7 in the shaft direction of the shaft 7 with respect to the supporting member 85 is stopped, and the movement of the supporting member 85 with respect to the shaft 7 is started. In other words, the driving by the motor 30 is switched from the movement of the shaft 7 to the movement of the supporting member 85. For example, after the movement of the supporting member 85 is started, when the supporting member 85 is moved to a predetermined position, the driving of the motor 30 is stopped.

In this manner, the movement of the optometry unit 50 to the examination position is completed. For example, the switching mechanism from the movement of the shaft 7 to the movement of the supporting member 85 can be used as a contact restraining mechanism in a case where the optometry unit 50 is in contact with another member when the optometry unit 50 is moving to the examination position.

For example, the operation in which a state where the optometry unit 50 is disposed in the examination position as illustrated in FIG. 3B becomes a state where the optometry unit 50 is disposed in the retreat position as illustrated in FIG. 3A will be described. For example, as the motor 30 negatively rotates, the shaft 7 rotates. As the shaft 7 rotates, for example, the shaft 7 moves in the shaft direction of the shaft 7 with respect to the supporting member 85 and the part protruding from the supporting member 85 in the shaft 7 decreases (the shaft 7 becomes shorter). For example, in conjunction with the movement in which the shaft 7 increases, the supporting member 85 rotates in a direction of an arrow B around the rotary axis R1. Similar to the description above, as the supporting member 85 rotates around the rotary axis R1, the connecting portion 5 connected to the holding arm 35 rotates in the direction of the arrow B around the rotary axis R2, and the optometry unit 50 connected to the connecting portion 5 rotates in the direction of the arrow B. Further, for example, the connecting portion 5 rotates with respect to the holding arm 35 such that the optometry unit 50 can maintain a vertical state by the own weight of the optometry unit 50. Accordingly, for example, the optometry unit 50 moves from the examination position as illustrated in FIG. 3B to the retreat position as illustrated in FIG. 3A. In other words, the optometry unit 50 can be moved upward.

Further, for example, the rotation (movement to the retreat position) of the optometry unit 50 in a B direction is stopped when the optometry unit 50 reaches the retreat position by the block 32 and the block receiver 39. For example, with the driving of the motor 30, the block 32 is rotated in the B direction around the rotary axis R2 and comes into contact with the block receiver 39 when the optometry unit 50 reaches the retreat position. For example, as the block 32 comes into contact with the block receiver 39, the rotation is stopped. For example, as the block 32 is stopped, the rotation of the supporting member 38 connected to the block 32 is stopped. In addition, according to this, the rotation of the shaft 7 and the supporting member 85 is also stopped. According to this, the optometry unit 50 is stopped in the retreat position. In other words, the optometry unit 50 is stopped in the retreat position by the block 32 and the block receiver 39. In this manner, the movement of the optometry unit 50 to the retreat position is completed.

In addition, in the present example, the configuration in which the movement of the optometry unit 50 to the retreat position is stopped by the block 32 and the block receiver 39 has been described as an example, but the invention is not limited thereto. For example, a detection portion for detecting a retreat state may be provided, and the movement of the optometry unit 50 to the retreat position may be stopped based on the detection result. In this case, as an example, for example, a shielding portion is provided in the supporting member 38 and a detector is provided on the base 31. For example, in a case where the optometry unit 50 is positioned in the retreat position, and in a case where the shielding portion provided in the supporting member 38 is detected by the detector, the movement of the optometry unit 50 to the retreat position may be stopped.

<First Operation Portion and Second Operation Portion>

Hereinafter, the first operation portion 8 and the second operation portion 9 will be described. For example, the first operation portion 8 is a vertical movement switch (movement switch of the optometry unit 50). In addition, for example, the second operation portion 9 is a vertical movement switch (movement switch of the optometry unit 50). In other words, in the present example, the first operation portion 8 and the second operation portion 9 are operation means for performing the same operation. For example, by operating the first operation portion 8 or the second operation portion 9, it is possible to move the optometry unit 50 between the examination position in front of the subject eye and the retreat position.

For example, the first operation portion 8 is disposed on the left surface of the housing 2. For example, the second operation portion 9 is disposed on the right surface of the housing 2. For example, the first operation portion 8 and the second operation portion 9 are disposed above the left and right surfaces. In addition, in the present example, for example, the first operation portion 8 and the second operation portion 9 are disposed at symmetrical positions with respect to the center of the housing 2 as a reference.

In addition, in the present example, for example, the first operation portion 8 and the second operation portion 9 are operation means having the same shape. For example, since the first operation portion 8 and the second operation portion 9 have the same shape, when operating one of the first operation portion 8 or the second operation portion 9, the subjective optometry apparatus 1 can be operated by the same operation as the other operation, and thus, it is possible to suppress the possibility that an examiner performs an erroneous operation and it becomes easy to perform the operation.

In addition, in the present example, a configuration in which the first operation portion 8 and the second operation portion 9 are provided as the operation means for moving the optometry unit 50 between the examination position in front of the subject eye and the retreat position is employed, but the invention is not limited thereto. For example, the operation means for moving the optometry unit 50 between the examination position in front of the subject eye and the retreat position may be configured to have at least one operation means. As an example, in a case where one operation means is used, the operation means may be disposed at a position where the operation from the left and right sides of the subjective optometry apparatus 1 is possible.

<Light Projecting Optical System>

Figure 4A:
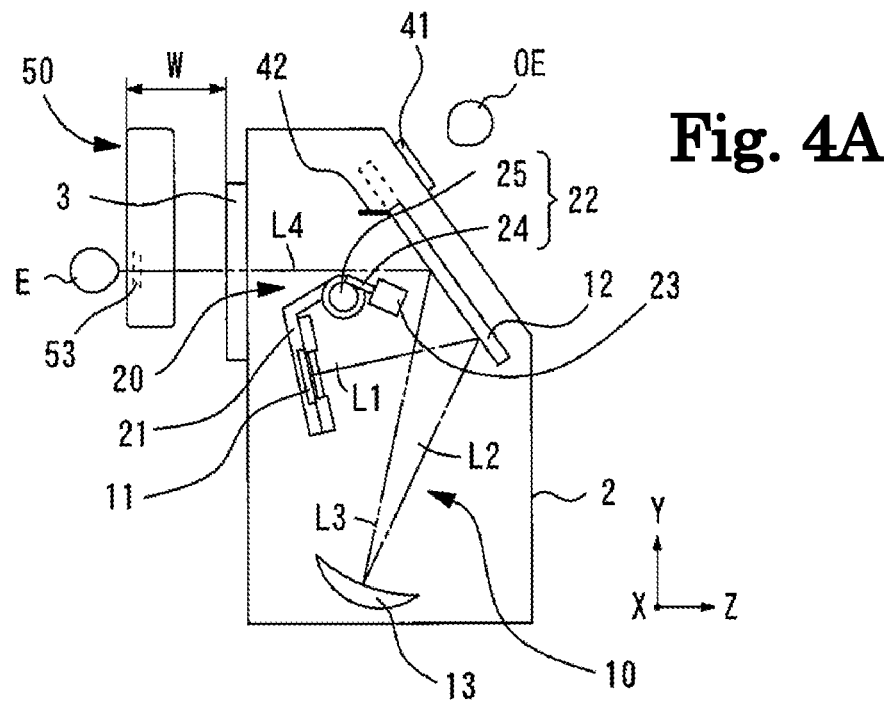
FIGS. 4A and 4B are views of a light projecting optical system when viewed from a left side.
Figure 4B:
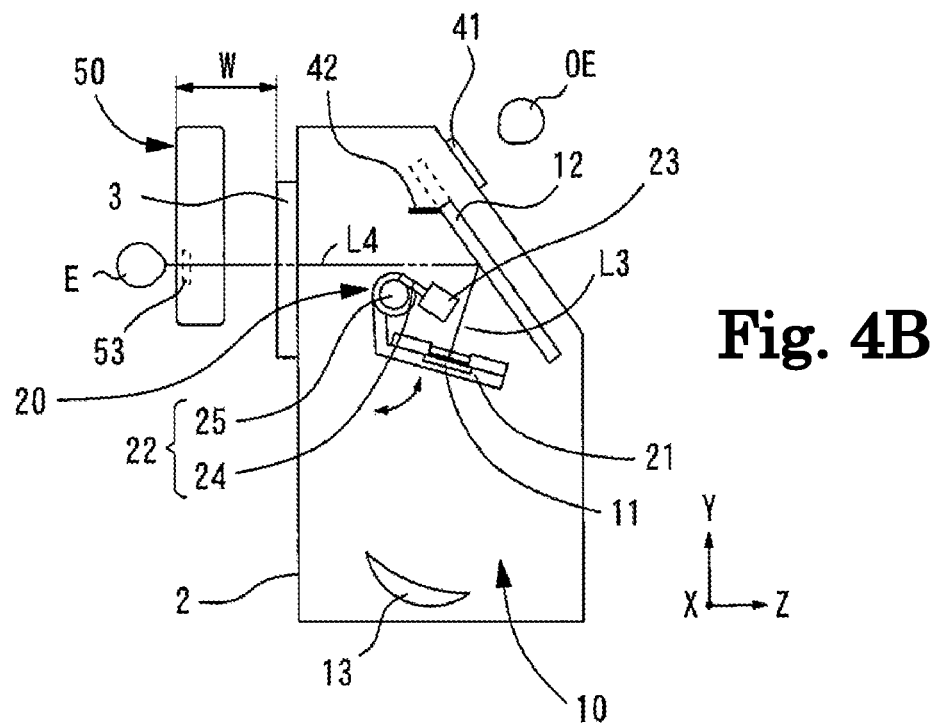

Hereinafter, the light projecting optical system 10 will be described. For example, FIGS. 4A and 4B are views of the light projecting optical system 10 when viewed from the left surface (arrow direction C1 in FIGS. 1A and 1B). FIG. 4A illustrates the optical disposition at the time of a far examination. FIG. 4B illustrates the optical disposition at the time of a near examination. For example, the light projecting optical system 10 has a visual target presenting portion and projects the target light flux emitted from the visual target presenting portion toward a subject eye E. For example, in the present example, a display (for example, a display 11) is used as a visual target presenting portion. For example, the light projecting optical system 10 includes the display 11, the flat surface mirror 12, a concave surface mirror 13, a far-near switching portion 20, and the like.

For example, an examination visual target, such as a Landolt ring visual target or a fixation target, is displayed on the display 11. For example, the display on the display 11 is controlled by the control portion 80 to be described later. For example, a liquid crystal display (LCD), an organic electroluminescence (EL), a plasma display or the like may be used as the display.

For example, at the time of the far examination illustrated in FIG. 4A, a screen of the display 11 is oriented to a far side of the housing 2, and the target light flux is emitted rearward. In addition, the target light flux may be emitted in a horizontal direction (Z direction) from the display or may be emitted in an oblique direction (YZ direction). For example, at the time of the near examination illustrated in FIG. 4B, the screen of the display 11 is oriented to an upper side, and the target light flux is emitted upward. In addition, the target light flux may be emitted in a vertical direction (Y direction) from the display or may be emitted in the oblique direction (YZ direction). In this manner, the target light flux from the display 11 is projected toward the subject eye E.

For example, the flat surface mirror 12 reflects the target light flux from the display 11 and guides the target light flux to the concave surface mirror 13. In addition, for example, the flat surface mirror 12 reflects the target light flux from the display 11 and guides the target light flux to the subject eye E. For example, in the flat surface mirror 12, the mirror coating is performed only to the lower part (the solid line part of the flat surface mirror 12 in FIGS. 4A and 4B) and the mirror coating is not performed to the upper part (the dotted line part of the flat surface mirror 12 in FIGS. 4A and 4B).

Therefore, in the present example, the upper part of the flat surface mirror 12 is transparent. For example, the focal length of the flat surface mirror 12 at the time of the near examination is designed such that the optical distance from the display to the subject eye E is 40 cm. In addition, in the present example, the target light flux may be capable of being reflected, and is not limited to the configuration using the flat surface mirror. For example, a reflection member may be employed. In this case, for example, a configuration using a prism, a beam splitter, a half mirror, or the like may be used.

For example, the concave surface mirror 13 reflects the target light flux from the display 11 toward the flat surface mirror 12. For example, the concave surface mirror 13 sets the presentation distance of the examination visual target displayed on the display 11 as the far examination distance. For example, the focal length of the concave surface mirror 13 is designed such that the optical distance from the display 11 to the subject eye E is 5 m. In addition, in the present example, the configuration is not limited to the configuration in which the concave surface mirror 13 is used. For example, the reflection member capable of reflecting the target light flux may be employed. In this case, for example, a configuration using a non-spherical surface mirror, free curved surface mirror, or the like is used may be employed. In addition, for example, the configuration in which the lens is used may be employed. In this case, for example, a configuration in which, when the target light flux is projected onto the subject eye E from the display 11 via the lens, the optical distance from the display 11 to the subject eye E is designed to be 5 m by the lens may be employed.

For example, at the time of the far examination illustrated in FIG. 4A, the target light flux is emitted from the display 11 and is projected onto the subject eye E of the examinee passing through the optical members in the order of the flat surface mirror 12, the concave surface mirror 13, and the flat surface mirror 12. In other words, when the target light flux emitted from the display 11 is incident on the flat surface mirror 12 through an optical axis L1, the target light flux is reflected in an optical axis L2 direction and is oriented to the concave surface mirror 13. When the target light flux is incident on the concave surface mirror 13, the target light flux is reflected in an optical axis L3 direction and is oriented to the flat surface mirror 12. Furthermore, when the target light flux is incident on the flat surface mirror 12, the target light flux is reflected in an optical axis L4 direction and is projected onto the subject eye E of the examinee. In addition, for example, at the time of the near examination illustrated in FIG. 4B, the target light flux emitted from the display 11 and reflected to the flat surface mirror 12 is projected onto the subject eye E of the examinee. In other words, when the target light flux emitted from the display 11 is incident on the flat surface mirror 12 through the optical axis L3, the target light flux is reflected in the optical axis L4 direction and is projected onto the subject eye E of the examinee. For example, in this manner, the light projecting optical system 10 emits the target light flux from the inside to the outside of the housing 2.

For example, the far-near switching portion 20 changes the position of the display 11 at the time of the far examination and the near examination. For example, the far-near switching portion 20 includes a holding portion 21, a gear 22, a motor 23, and the like. For example, the holding portion 21 holds the display 11. For example, the gear 22 has a worm portion 24 and a wheel portion 25. For example, the worm portion 24 and the wheel portion 25 are formed of gears that mesh with each other. For example, the motor 23 is connected to the worm portion 24, and the holding portion 21 is connected to the wheel portion 25. For example, the worm portion 24 rotates as the motor 23 is driven, and accordingly, the wheel portion 25 rotates in the arrow direction. Accordingly, it is possible to integrally move the display 11 together with the holding portion 21, and to switch the presentation position of the examination visual target displayed on the screen of the display 11 at the time of the far examination and the near examination. In addition, the gear 22 and the motor 23 are disposed on the side wall of the housing 2 and are disposed at positions which do not obstruct the target light flux oriented from the display 11 to the subject eye E.

In addition, in the present example, an example in which the optical axis L3 and the optical axis L4 of the light projecting optical system 10 are coaxial at the time of the far examination and the near examination has been described as an example, but the invention is not limited thereto. For example, in the present example, the target light flux may be capable of being guided to the subject eye E, and may be configured to pass through different optical paths at the time of the far examination and the near examination.

<Observation Unit>

Figure 5:
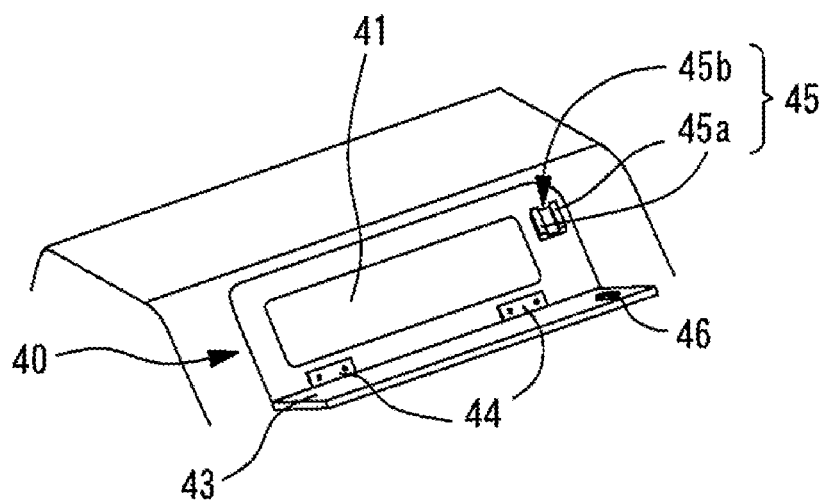
FIG. 5 is a view for describing an observation unit.

Hereinafter, the observation unit 40 will be described. FIG. 5 is a view for describing the observation unit. For example, the observation unit 40 in the present example is used for observing the positional relationship between the optometry unit 50 and the subject eye E which will described later via the presentation window 3. For example, in the present example, the observation unit 40 includes the observation window 41, a shielding portion 42, a cover 43, a detector (a detection portion) 45, and the like. In addition, the observation unit 40 may be configured to include at least the observation window 41.

For example, the observation window 41 is used for observing the positional relationship between the optometry unit 50 and the subject eye E via the presentation window 3 from the outside of the housing 2. For example, the observation window 41 in the present example is disposed at a position where it is possible to confirm a pupil position of the subject eye E from an examiner eye OE. For example, in a case where the examiner looks into the observation window 41, the flat surface mirror 12 is formed transparent in a region through which the line of sight of the examiner passes such that the line of sight of the examiner is not blocked by the flat surface mirror 12. For example, the shielding portion 42 suppresses the target light flux from the light projecting optical system 10 from entering the observation window 41. For example, in the present example, the shielding portion 42 is disposed at the boundary between the transparent portion and the mirror portion of the flat surface mirror 12.

For example, the cover 43 is fixed to the housing 2 by a hinge 44, and can be opened and closed with respect to the observation window 41. For example, the cover 43 can be opened and closed as the examiner pushes and pulls a knob (not illustrated).

For example, the detector 45 detects the opening and closing of the cover 43 in the observation unit 40. For example, the detector 45 is configured using an optical sensor, such as a photo interrupter. In other words, the detector 45 in the present example has a projection portion 45a in which the light emitting element and the light receiving element oppose each other, and a protrusion portion 46 provided on the cover 43 is fitted into the recess portion 45b. For example, the detector 45 detects that the cover is in a closed state when the light from the light emitting element is shielded by making the protrusion portion 46 fitted into the recess portion 45b. In addition, for example, the detector 45 detects that the cover is in an opened state when the protrusion portion 46 is separated from the recess portion 45b and the light from the light emitting element is received by the light receiving element.

<Optometry Unit>

Hereinafter, the optometry unit 50 will be described. For example, the optometry unit 50 is close to the housing 2 (refer to FIGS. 4A and 4B). For example, in the present example, a distance W (refer to FIGS. 4A and 4B) from the examination window 53 in the optometry unit 50 to the presentation window 3 disposed in the housing 2 is designed to be approximately 135 mm. In addition, the distance W from the examination window 53 to the presentation window 3 is not limited to the present example. For example, in a case where the distance W is shorter than a head length of the examiner, it is not possible for the examiner to insert the head between the optometry unit 50 and the housing 2, and thus, it becomes difficult to observe the positional relationship between the optometry unit 50 and the subject eye E. Therefore, in a case where the distance W is shorter than the head length of the examiner, it is possible to effectively use the observation window 41.

Figure 6:
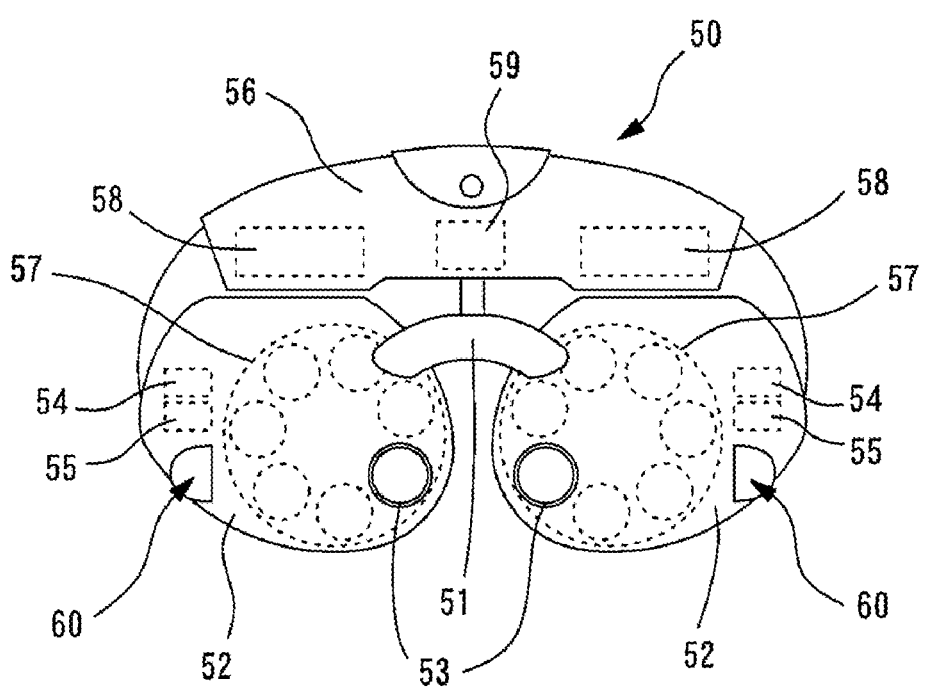
FIG. 6 is a view illustrating an optometry unit.

For example, FIG. 6 is a view illustrating the optometry unit 50. For example, the optometry unit 50 includes a forehead rest 51, a pair of left and right lens chamber units 52, the examination window 53, a driving portion 54, a driving portion 55, a moving unit 56, a cornea position aiming optical system 60, and the like. For example, the forehead rest 51 abuts against the forehead of the examinee and is used for keeping the distance between the subject eye E and the optometry unit 50 constant.

For example, the lens chamber unit 52 switches and disposes the optical element in the examination window 53. For example, a lens disk 57 is provided on the inside of the lens chamber unit 52. The lens disk 57 disposes a large number of optical elements (a spherical lens, a cylindrical lens, a dispersing prism, and the like) on the same circumference. For example, the lens disk 57 is rotationally controlled by the driving portion 54 (an actuator and the like). Accordingly, the optical element desired by the examiner is disposed in the examination window 53. For example, the optical element disposed in the examination window 53 is rotationally controlled by the driving portion 55 (a motor, a solenoid, and the like). Accordingly, the optical element is disposed in the examination window 53 by a rotation angle desired by the examiner.

For example, the lens disk 57 is configured of one lens disk or a plurality of lens disks. For example, in a case where the plurality of lens disks (lens disk groups) are provided, a driving portion that corresponds to each lens disk is provided. For example, each lens disk of the lens disk group includes an opening (or a 0D lens) and a plurality of optical elements. As a type of each of the lens disks, a spherical lens disk having a plurality of spherical lenses with different frequencies, a cylindrical lens disk having a plurality of cylindrical lenses with different frequencies, and an auxiliary lens disk are representative. Further, the lens disk in the present example includes a positioning lens with a cross hatched line. For example, at least one of a red filter and a green filter, a prism, a cross cylinder lens, a polarizing plate, a Maddox lens, and an autocross cylinder lens is disposed on the auxiliary lens disk. In addition, for the detailed configuration of the lens disk, it is desired to refer to JP-A-2007-68574 and JP-A-2011-72431.

For example, the moving unit 56 adjusts an interval between the lens chamber units 52. For example, the interval between the left and right lens chamber units is adjusted by the driving portion 58 having a slide mechanism. Accordingly, the interval of the examination window 53 can be changed according to a PD of the subject eye. Further, the moving unit 56 adjusts a convergence angle (inside angle) of the left and right lens chamber units. For example, the convergence angle of the left and right optometry unit is adjusted by a driving portion 59 having a convergence mechanism. In addition, for the detailed configuration of the moving unit, it is desired to refer to JP-A-2004-329345.

In addition, the optometry unit 50 is not limited to the above-described configuration. For example, the optometry unit 50 may be configured to change the optical characteristics (for example, at least any one of a spherical power, a cylindrical power, a cylindrical axis, polarization characteristics, and the amount of aberration) of the target light flux. For example, as a configuration in which the optical characteristics of the target light flux is changed, a configuration in which an optical element is controlled may be employed. For example, a configuration using a wavefront modulation element may be employed.

<Control Portion>

Figure 7:
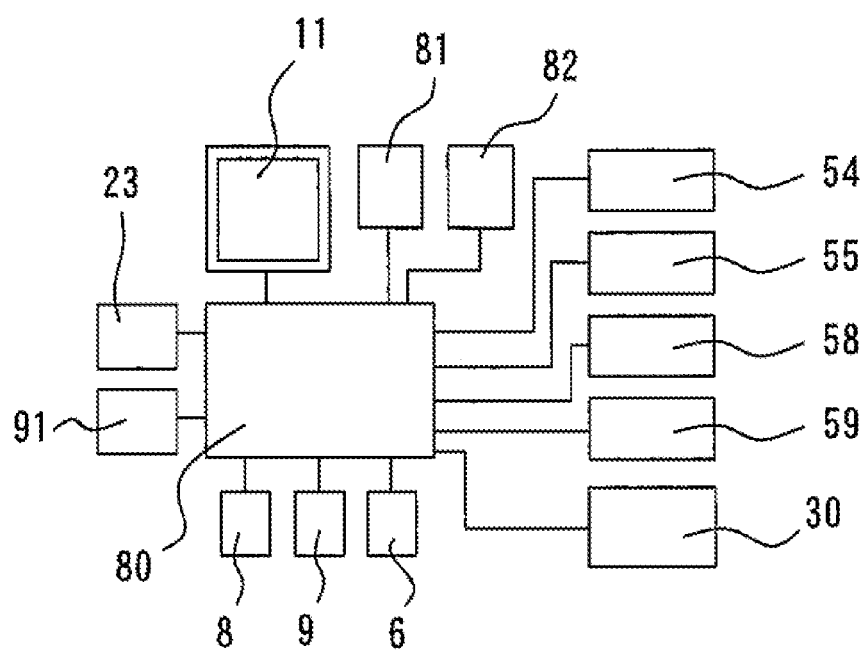
FIG. 7 is a schematic configuration view of a control system in a subjective optometry apparatus.

For example, FIG. 7 is a schematic configuration view of a control system in the subjective optometry apparatus 1. For example, the first operation portion 8, the second operation portion 9, the display 11, the detector 45, a controller 81, a non-volatile memory 82, a light source 91, and the like are connected to the control portion 80. In addition, for example, the motor 30 included in the moving unit 6, the motor 23 included in the far-near switching portion 20, and the driving portion (driving portions 54, 55, 58, and 59) of each member of the optometry unit 50 and the like, are connected to the control portion 80.

For example, the control portion 80 includes a CPU (processor), a RAM, a ROM, and the like. For example, the CPU controls each member of the subjective optometry apparatus 1. For example, the RAM temporarily stores various pieces of information. For example, various programs for controlling the operation of the subjective optometry apparatus 1, examination visual target data, and the like, are stored in the ROM. Meanwhile, the control portion 80 may be configured with a plurality of control portions (that is, a plurality of processors).

For example, the controller 81 is used when switching the display of the display 11 in the light projecting optical system 10, disposition of the optical elements in the optometry unit 50, and the like. For example, a signal input from the controller 81 is input to the control portion 80 via a cable (not illustrated). In addition, in the present example, the signal from the controller 81 may be input to the control portion 80 via wireless communication, such as infrared rays.

For example, the non-volatile memory 82 is a non-fugitive storage medium capable of holding stored contents even when the supply of power is stopped. For example, as the non-volatile memory 82, a hard disk drive, a flash ROM, the subjective optometry apparatus, and a USB memory, or the like can be used. For example, the non-volatile memory 82 stores multiple pieces of the examination visual target data, such as Landolt ring visual target (for example, visual target data of visual acuity values 0.1 to 2.0).

For example, in the present example, the control portion 80 switches a measurement mode of the subjective optometry apparatus 1 based on the detection result of the detector 45. For example, in the present example, the control portion 80 automatically switches the measurement mode in conjunction with the opening and closing of the cover 43. For example, when the detector 45 detects that the cover 43 is opened, the control portion 80 sets the measurement mode to a second mode for confirming the pupil position of the examinee. In addition, for example, when the detector 45 detects that the cover 43 is closed, the control portion 80 sets the measurement mode to a first mode for subjectively examining the examinee. In addition, in the present example, the configuration in which the measurement mode is automatically switched in conjunction with the opening and closing of the cover 43 is employed, but the invention is not limited thereto. For example, the switching of the measurement mode may be performed manually by the examiner. In this case, a signal for switching the measurement mode may be input to the control portion 80 by using the controller 81 which will be described later.

<Examination Operation>

An examination operation of the subjective optometry apparatus 1 having the above-described configuration will be described. In addition, in the present example, a case of measuring the subjective eye refractive power in the near distance viewing state will be described as an example. In other words, in the present example, a case where near subjective examination (near examination) is performed and the near distance subjective eye refractive power is measured will be described as an example.

Figure 8:
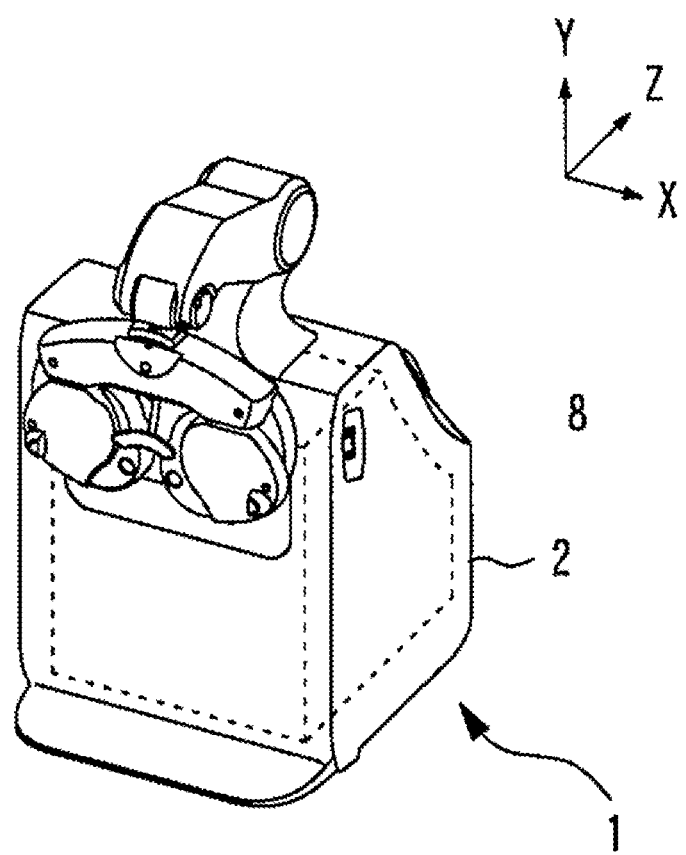
FIG. 8 is a view illustrating a state where subjective examination using the optometry unit is possible.

Initially, for example, the examiner operates the first operation portion 8 to lower the optometry unit 50 to the examination position illustrated in FIG. 8. For example, when the first operation portion 8 is operated, the control portion 80 drives the motor 30. For example, by driving the motor 30, the optometry unit 50 is lowered toward the examination position. For example, when the optometry unit 50 is moved to the examination position by driving the motor 30, the block 32 and the block receiver 36 come into contact with each other and the lowering of the optometry unit 50 is stopped. In addition, together with the stop of the optometry unit 50, the movement of the supporting member 85 is started, and when the supporting member 85 is moved to a predetermined position, the driving of the motor 30 is stopped. Accordingly, as illustrated in FIG. 8, the movement of the eye refractive power measurement unit 50 to the examination position is completed, and the subjective examination using the optometry unit 50 becomes possible.

In this manner, the optometry unit 50 moves to the examination position. Next, for example, the examiner measures the PD of the examinee in advance before performing the subjective examination, and inputs the measured PD in the subjective optometry apparatus 1. Accordingly, the control portion 80 drives the driving portion 58, adjusts the interval between the left and right lens chamber units 52, and changes the interval of the examination window 53 in accordance with the PD of the subject eye. For example, the control portion 80 performs adjustment such that the distance in the horizontal direction (X direction) between the optical axes of the left and right examination windows 53 becomes the same as the PD. In addition, in the present example, the expression "the same" also includes being substantially the same.

Next, the examiner instructs the examinee to look into the examination window 53. Here, for example, the examiner opens the cover 43 for confirming a pupillary distance PD of the subject eye E. At this time, when the detector 45 detects that the cover 43 is opened, the control portion 80 switches the measurement mode to the second mode for confirming the pupil position of the examinee.

For example, the examiner adjusts the interval between the left and right lens chamber units 52 by operating the controller 81 as necessary. Next, in order to confirm a cornea apex position of the subject eye F, the examiner performs positioning the subject eye E with respect to the eye refractive power measurement unit 50 by using the cornea position aiming optical system 60.

For example, when the positioning of the subject eye E to the optometry unit 50 is completed, the examiner closes the cover 43 and starts the subjective examination. At this time, the detector 45 detects that the cover 43 is closed, and the control portion 80 switches the measurement mode to the first mode for subjectively examining the examinee.

For example, when the controller 81 is operated by the examiner and a near mode for performing the near subjective examination is selected, the setting for performing the near subjective examination is performed. For example, in a case of performing the near examination (refer to FIG. 4B), the display 11 moves together with the holding portion 21 and is disposed close to the subject eye E (for example, a distance of 40 cm away). From the display 11, the target light flux is emitted toward the flat surface mirror 12. The target light flux is reflected by the flat surface mirror 12 and guided to the subject eye E. In addition, for example, in a case of performing the far examination (refer to FIG. 4A), the control portion 80 turns on the display 11. For example, from the display 11 held by the holding portion 21, the target light flux is emitted toward the flat surface mirror 12. The target light flux is reflected by the flat surface mirror 12 and the concave surface mirror 13, respectively, and guided to the subject eye E via the flat surface mirror 12 again.

Here, for example, in the present example, the control portion 80 controls the operation when acquiring the near distance subjective eye refractive power which is the subjective eye refractive power of the subject eye in the near distance viewing state based on the near distance objective eye refractive power. For example, in the present example, as a configuration for controlling the operation when acquiring the near distance subjective eye refractive power, a configuration in which the control portion 80 performs the setting of the initial value when performing the near subjective examination will be described as an example. Hereinafter, the setting of the initial value when performing the near subjective examination will be described.

<Initial Value Setting>

For example, in the present example, in the subjective optometry apparatus 1, when starting the subjective measurement of the eye refractive power of the subject eye in the near subjective examination, the near distance objective eye refractive power obtained by objectively measuring the eye refractive power of the subject eye in the near distance viewing state is acquired. FIG. 9 is a view for describing the setting of the initial value.

In the present example, for example, the objective eye refractive power measurement apparatus (ophthalmologic apparatus) 100 and the subjective optometry apparatus 1 are connected to each other in a wireless manner. Accordingly, the data can be transmitted and received between the objective eye refractive power measurement apparatus (ophthalmologic apparatus) 100 and the subjective optometry apparatus 1. It is needless to say that the objective eye refractive power measurement apparatus 100 and the subjective optometry apparatus 1 may be connected to each other in a wireless manner and in a wired manner.

For example, the objective eye refractive power measurement apparatus (ophthalmologic apparatus) 100 presents a fixation target at a near presentation distance to the subject eye, irradiates the subject eye with the measurement light by an objective measurement optical system, and measures the near distance objective eye refractive power by receiving the reflected light from the subject eye by the light receiving element. In addition, for example, the objective eye refractive power measurement apparatus 100 presents a fixation target at a far presentation distance to the subject eye, irradiates the subject eye with the measurement light by the objective measurement optical system, and measures the far distance objective eye refractive power by receiving the reflected light from the subject eye by the light receiving element. For example, these measured data are stored in the memory (not illustrated) of the objective eye refractive power measurement apparatus 100. For example, in the objective eye refractive power measurement apparatus 100, the measured data of the examinee may be stored in the memory (not illustrated) together with an ID of the examinee.

For example, in the subjective optometry apparatus 1, the controller 81 is operated by the examiner, and the ID of the examinee is input, and accordingly, the objective eye refractive power that corresponds to the ID of the examinee is received from the memory (not illustrated) of the objective eye refractive power measurement apparatus 100. For example, when receiving a patient ID input by the subjective optometry apparatus 1 from the subjective optometry apparatus 1, the objective eye refractive power measurement apparatus 100 calls the near distance objective eye refractive power that corresponds to the patient ID from the memory (not illustrated), and sends the near distance objective eye refractive power toward the subjective optometry apparatus 1.

For example, the control portion 80 receives the near distance objective eye refractive power transmitted from the objective eye refractive power measurement apparatus 100. Accordingly, the control portion 80 can acquire the near distance objective eye refractive power of the examinee. It is needless to say that the control portion 80 may receive and acquire the far distance objective eye refractive power together with the near distance objective eye refractive power. In addition, in the present example, a case where the objective eye refractive power measurement apparatus 100 is an apparatus different from the subjective optometry apparatus 1 has been described as an example, but the invention is not limited thereto. For example, an apparatus (for example, the subjective optometry apparatus 1) in which the subjective optometry apparatus 1 and the objective eye refractive power measurement apparatus 100 are integrally configured may also be employed. In this case, the objective eye refractive power measurement apparatus of the apparatus may measure the objective eye refractive power and may set the measured value as the initial value of the near subjective examination. For example, the control portion 80 may set the near distance objective eye refractive power as the initial value of the near subjective examination when acquiring the near distance objective eye refractive power. In other words, the control portion 80 controls the optometry unit 50 based on the near distance objective eye refractive power and sets the initial value. For example, the control portion 80 sets the initial value by setting the calibration power of the optometry unit 50 to a value that corresponds to the near distance objective eye refractive power.

In addition, for example, in a case where the far distance objective eye refractive power is acquired together with the near distance objective eye refractive power from the objective eye refractive power measurement apparatus 100, the objective eye refractive power used as the initial value may be manually selected and set. In addition, for example, the control portion 80 may be capable of automatically setting whether to use any objective eye refractive power of the far distance objective eye refractive power and the near distance objective eye refractive power as the initial value at the time of the subjective examination, in accordance with which examination mode of the near examination mode and the far examination mode is set. In addition, in the present example, a configuration of the automatic setting is described as an example.

For example, the control portion 80 sets the near distance objective eye refractive power as the initial value in a case where the near examination mode is set. For example, in the present example, a case where the spherical power, the astigmatic power, and the astigmatic axis angle are respectively set as parameters of the eye refractive power used for setting the initial value is described as an example. In addition, in the present example, the eye refractive power used for setting the initial value is not limited thereto. For example, as the eye refractive power used for setting the initial value, only the astigmatism information of the astigmatic power and the astigmatic axis angle may be used. In other words, for example, as the parameter of the eye refractive power used for setting the initial value, at least any one of the spherical power, the astigmatic power, and the astigmatic axis angle may be used.

For example, when the optometry unit 50 is controlled by the control portion 80 and the setting of the initial value is completed, the examiner performs the near examination of the subject eye while changing the examination visual target together with the change of the calibration power of the optometry unit 50.

For example, at the time of the near examination, the examiner operates the controller 81 and displays the examination visual target on the screen of the display 11. In accordance with the input signal from the controller 81, the control portion 80 calls the corresponding examination visual target data from the non-volatile memory 82 and controls the display on the display 11. The examination visual target displayed on the display 11 is presented to the subject eye E of the examinee via the examination window 53 in the optometry unit 50 and the presentation window 3. For example, the examiner asks the examinee how the visibility of the examination visual target while switching the examination visual target. As an example, for example, the examiner performs switching to the visual target having a visual acuity value higher by one step in a case where the answer of the examinee is a correct answer. In addition, as an example, for example, the examiner performs switching to the visual target having a visual acuity value lower by one step in a case where the answer of the examinee is a wrong answer. In addition, for example, the examiner switches the visual target and performs the examination while changing the calibration power for the examination visual target displayed on the screen. In this manner, the examiner can acquire the subjective eye refractive power (for example, a spherical power S, an astigmatic power C, an astigmatic axis angle A, and the like) and the like in the near distance viewing state of the subject eye.

For example, when the near examination or the far examination is completed, the examiner performs provisional frame examination with respect to the subject eye. For example, the examiner operates an upper switch 8a of the first operation portion 8 to raise the optometry unit 50 to the retreat position illustrated in FIGS. 1A and 1B. For example, when the upper switch 8a of the first operation portion 8 is operated, the control portion 80 drives the motor 30. In addition, for example, in a case of moving the optometry unit 50 to the retreat position, the control portion 80 rotates the motor 30 in a rotation direction opposite to the rotation direction of the motor 30 in a case of moving the optometry unit 50 to the examination position.

For example, when the movement of the optometry unit 50 to the retreat position is completed, the examiner mounts a provisional frame (a trial frame or a test case) on the examinee and confirms the mounting feeling while exchanging lenses (trial lenses) having various degrees.

As described above, for example, the subjective optometry apparatus includes the acquisition portion for acquiring the near distance objective eye refractive power which is an eye refractive power of the subject eye objectively measured in the near distance viewing state, and the control portion for controlling the operation for acquiring the near distance subjective eye refractive power which is the subjective eye refractive power of the subject eye measured in the near distance viewing state, based on the near distance objective eye refractive power. Accordingly, for example, based on the near distance objective eye refractive power, it is possible to perform the subjective examination in the near distance viewing state taking into account the near distance objective eye refractive power by controlling the operation when acquiring the near distance subjective eye refractive power which is the subjective eye refractive power of the subject eye.

In addition, for example, the control portion may set the near distance objective eye refractive power as the initial value of the calibration portion when the control portion acquires the near distance subjective eye refractive power. According to this, for example, it is possible to perform the subjective examination in the near distance viewing state with the near distance objective eye refractive power as the initial value. Therefore, it becomes possible to start the subjective examination of the near distance viewing state from the result of the near distance objective eye refractive power, and it becomes possible to rapidly acquire the near distance eye refractive power. In addition, since it is possible to acquire the near distance subjective eye refractive power with the near distance objective eye refractive power as the initial value, it is possible to acquire the near distance subjective eye refractive power with higher accuracy.

In addition, for example, the control portion may set at least the near distance objective astigmatism information indicating the near distance objective eye refractive power as the initial value in the calibration portion when the control portion acquires the near distance subjective eye refractive power. Accordingly, for example, it is ascertained that there is a difference in measurement results between the near distance objective eye refractive power which is objectively measured in the near distance viewing state and the far distance objective eye refractive power measured in the far distance viewing state, particularly in the astigmatism information. Therefore, by controlling the operation of the subjective optometry apparatus in consideration of the near distance objective astigmatism information, more appropriate operation can be performed.

Modification Example

In addition, in the present example, as a configuration for controlling the operation when acquiring the near distance subjective eye refractive power, a configuration for setting the initial value when performing the near subjective examination has been described as an example, but the invention is not limited thereto. For example, as a configuration for controlling the operation when acquiring the near distance subjective eye refractive power, the control portion 80 may acquire the far distance subjective eye refractive power which is the subjective eye refractive power of the subject eye in the far distance viewing state, may set at least any parameter of the far distance subjective eye refractive power to be changeable to the corresponding parameter in the far distance objective eye refractive power based on the comparison result of the near distance objective eye refractive power and the far distance subjective eye refractive power, and may acquire the near distance subjective eye refractive power based on the far distance subjective eye refractive power. Hereinafter, a more detailed description will be given.

Figure 10A:
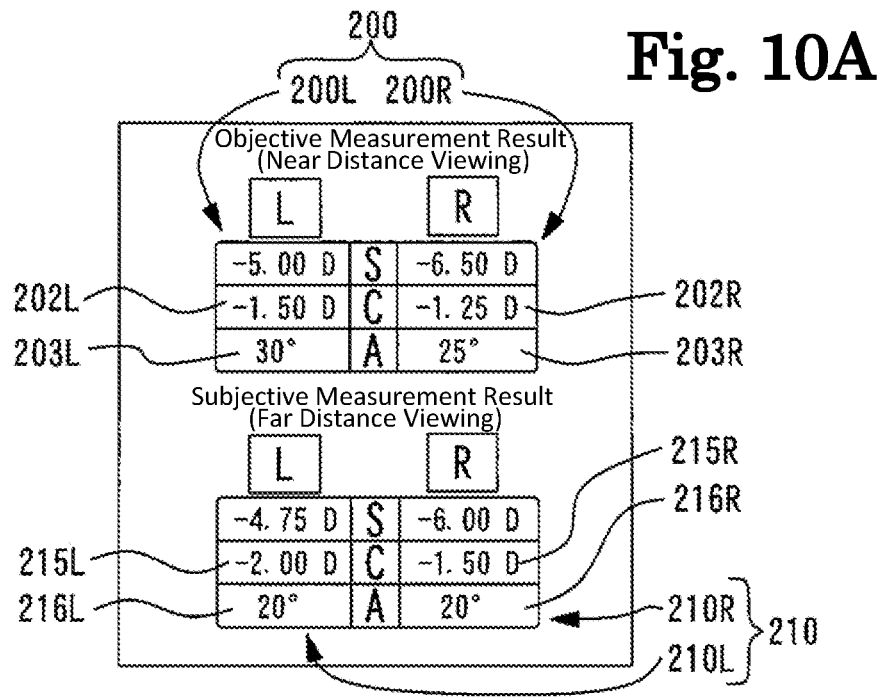
FIGS. 10A and 10B are views for describing a change of parameters of a near distance objective eye refractive power and a far distance subjective eye refractive power.
Figure 10B:
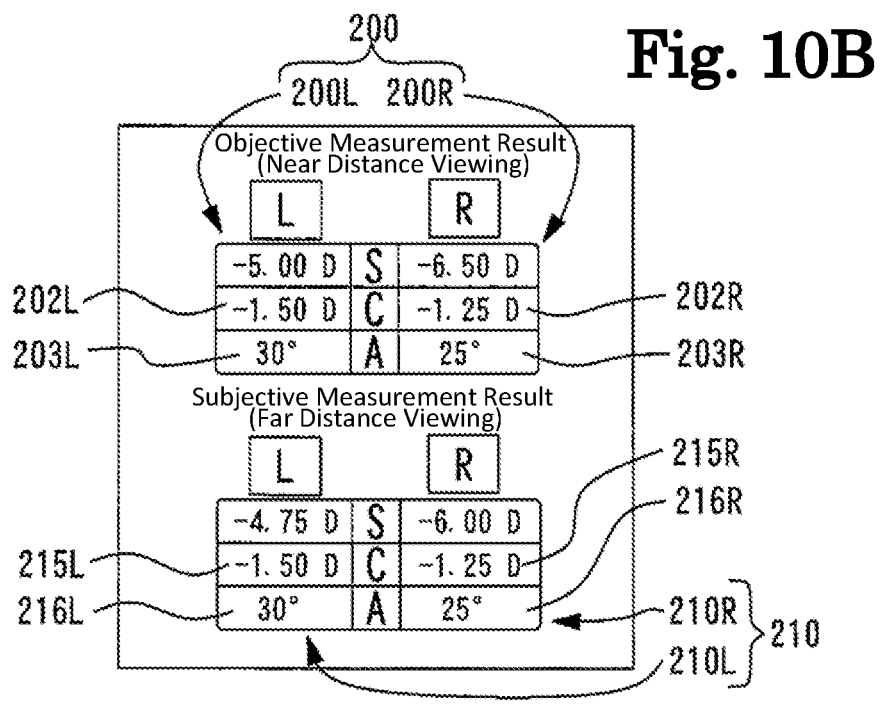

FIGS. 10A and 10B are views for describing a change in parameters of the near distance objective eye refractive power and the far distance subjective eye refractive power. In addition, in the present example, a case of changing the astigmatism information as the change of the parameter will be described as an example. In other words, for example, a case where the far distance subjective astigmatism information of the far distance subjective eye refractive power and the near distance objective astigmatism information of the near distance objective eye refractive power are changed to each other has been described as an example. For example, FIG. 10A is a view illustrating a state before the far distance subjective astigmatism information of the far distance subjective eye refractive power and the near distance objective astigmatism information of the near distance objective eye refractive power are changed to each other. For example, FIG. 10B is a view illustrating a state after the far distance subjective astigmatism information of the far distance subjective eye refractive power and the near distance objective astigmatism information of the near distance objective eye refractive power are changed to each other. In addition, in the present example, a configuration in which the far distance subjective astigmatism information (for example, the far distance subjective astigmatic power and the far distance subjective astigmatic axis angle) in the far distance subjective eye refractive power can be changed to the near distance objective astigmatism information (for example, the near distance objective astigmatic power and the near distance objective astigmatic axis angle) in the near distance objective eye refractive power has been described as an example.

For example, in the present example, the control portion 80 may acquire the near distance subjective eye refractive power based on the far distance subjective eye refractive power. For example, the examiner acquires the near distance objective eye refractive power of the examinee from the objective eye refractive power measurement apparatus 100. Further, for example, the examiner performs the setting to the far examination mode in the subjective optometry apparatus 1, and acquires the far distance subjective eye refractive power.

Next, the examiner operates the controller 81 and selects an acquisition switch (not illustrated) for acquiring the near distance subjective eye refractive power based on the far distance subjective eye refractive power. When the acquisition switch is selected, the control portion 80 acquires the comparison result of the near distance objective eye refractive power and the far distance subjective eye refractive power. In addition, in the present example, the difference information is used as the comparison result.

For example, the control portion 80 acquires the difference value between the near distance objective eye refractive power and the far distance subjective eye refractive power. In addition, for example, in the present example, the control portion 80 acquires the difference information between the left eye and the right eye, and sets whether to change the parameters or not. In addition, in the present example, for example, the control portion 80 acquires the difference value between the near distance objective astigmatic power (near distance objective astigmatic power 202L and 202R and near distance objective astigmatic power 202R and 202L) in near distance objective eye refractive power 200 (left eye near distance objective eye refractive power 200L and right eye near distance objective eye refractive power 200R), and the far distance subjective astigmatic power (far distance subjective astigmatic power 215L and 215R and far distance subjective astigmatic power 216L and 216R) in far distance subjective eye refractive power 210 (left eye far distance subjective eye refractive power 210L and right eye far distance subjective eye refractive power 210R).

For example, the control portion 80 acquires the difference information related on the left eye. For example, the control portion 80 acquires the difference information between the left eye near distance objective astigmatic power 202L (C=−1.50 D) and the left eye far distance subjective astigmatic power 215L (C=−2.00 D) (for example, the difference value of the astigmatic power) (refer to FIG. 10A). For example, when acquiring the difference information, the control portion 80 determines whether or not the difference information exceeds a predetermined threshold value.

For example, in a case where the difference information exceeds a predetermined threshold value, the control portion 80 changes the left eye far distance subjective astigmatism information (for example, the left eye far distance subjective astigmatic power 215L and a left eye far distance subjective astigmatic axis angle 216L) to the left eye near distance objective astigmatism information (for example, the left eye near distance objective astigmatic power 202L and a left eye near distance objective astigmatic axis angle 203L) in the near distance objective eye refractive power. In other words, the left eye far distance subjective eye refractive power 200L in FIG. 10A is changed to the left eye far distance subjective eye refractive power 200L in FIG. 10B. In this case, for example, the control portion 80 acquires the changed left eye far distance subjective eye refractive power 200L (left eye far distance subjective eye refractive power 200L in FIG. 10B) as the left eye near distance subjective eye refractive power. In addition, for example, as the threshold value, a threshold value for determining that it is necessary to change the parameter by simulation, experiment or the like may be set in advance. For example, a configuration may also be employed in which the threshold value can be set to any value by the examiner.

For example, in a case where the difference information does not exceed a predetermined threshold value, the control portion 80 does not change the left eye far distance subjective astigmatism information (for example, the left eye far distance subjective astigmatic power 215L and left eye far distance subjective astigmatic axis angle 216L) to the left eye near distance objective astigmatism information (for example, the left eye near distance objective astigmatic power of 202L and left eye near distance objective astigmatic axis angle 203L). In this case, for example, the control portion 80 acquires the left eye far distance subjective eye refractive power 200L (left eye far distance subjective eye refractive power 200L in FIG. 10A) which is not changed as the left eye near distance subjective eye refractive power.

In addition, for example, the control portion 80 acquires the difference information related on the right eye. For example, the control portion 80 acquires the difference information (for example, the difference value of the astigmatic power) between the right eye near distance objective astigmatic power 202R (C=−1.25 D) and the right eye far distance subjective astigmatic power 215R (C=−1.50 D) (refer to FIG. 10A). For example, when acquiring the difference information, the control portion 80 determines whether or not the difference information exceeds a predetermined threshold value.

For example, in a case where the difference information exceeds a predetermined threshold value, the control portion 80 changes the right eye far distance subjective astigmatism information (for example, the right eye far distance subjective astigmatic power 215R and a right eye far distance subjective astigmatic axis angle 216R) to the right eye near distance objective astigmatism information (for example, the right eye near distance objective astigmatic power 202R and the right eye near distance objective astigmatic axis angle 203R) in the near distance objective eye refractive power. In other words, the right eye far distance subjective eye refractive power 200R in FIG. 10A is changed to the right eye far distance subjective eye refractive power 200R in FIG. 10B. In this case, for example, the control portion 80 acquires the changed right eye far distance subjective eye refractive power 200R (right eye far distance subjective eye refractive power 200R in FIG. 10B) as the right eye near distance subjective eye refractive power.

In addition, for example, in a case where the difference information does not exceed a predetermined threshold value, the control portion 80 does not change the right eye far distance subjective astigmatism information (for example, the right eye far distance subjective astigmatic power 215R and the right eye far distance subjective astigmatic axis angle 216R) to the right eye near distance objective astigmatism information (for example, the right eye near distance objective astigmatic power 202R and the right eye near distance objective astigmatic axis angle 203R). In this case, for example, the control portion 80 acquires the right eye far distance subjective eye refractive power 200R (right eye far distance subjective eye refractive power 200R in FIG. 10A) which is not changed as the right eye near distance subjective eye refractive power.

In this manner, the near distance subjective eye refractive power of the left and right eyes is acquired. In this manner, for example, the control portion may acquire the far distance subjective eye refractive power which is the subjective eye refractive power of the subject eye in the far distance viewing state, may set at least any parameter of the far distance subjective eye refractive power to be changeable to the corresponding parameter in the far distance objective eye refractive power based on a comparison result of the near distance objective eye refractive power and the far distance subjective eye refractive power, and may acquire the near distance subjective eye refractive power based on the far distance subjective eye refractive power. Accordingly, for example, in a case of acquiring the near distance subjective eye refractive power based on the far distance subjective eye refractive power, by taking into account the near distance viewing state, it is possible to acquire the near distance subjective eye refractive power with higher accuracy. For example, in a case where there is a difference in the eye refractive power between the far distance viewing state and the near distance viewing state, in order to acquire the near distance subjective eye refractive power with higher accuracy, it is preferable to acquire the near distance subjective eye refractive power by taking into account the near distance viewing state. Therefore, for example, by changing the far distance subjective eye refractive power in accordance with the comparison result, it is possible to acquire the near distance subjective eye refractive power that has taken into account the near distance viewing state together with the far distance viewing state, and to acquire an excellent subjective eye refractive power.

In addition, for example, the comparison result may be a result of comparing at least the far distance subjective astigmatism information of the far distance subjective eye refractive power with the near distance objective astigmatism information of the near distance objective eye refractive power. Accordingly, for example, it is ascertained that there is a difference in measurement results between the near distance objective eye refractive power which is objectively measured in the near distance viewing state and the far distance subjective eye refractive power measured in the far distance viewing state, particularly in the astigmatism information. Therefore, for example, in a case of using the far distance subjective eye refractive power as the near distance subjective eye refractive power, it is easy to confirm whether or not the near distance viewing state is supposed to be considered by comparing the astigmatism information. Therefore, by comparing the astigmatism information, it is possible to easily confirm whether or not the near distance objective eye refractive power is acquired by taking into account the near distance viewing state with respect to the far distance subjective eye refractive power, and to more easily acquire the near distance subjective eye refractive power with higher accuracy.

In addition, in the present example, the difference information between the left eye and the right eye is calculated respectively, and it is set whether to change the parameters of the near distance objective eye refractive power and the far distance subjective eye refractive power, but the invention is not limited thereto. For example, the difference information of one of the left eye and the right eye may be acquired, and whether to change the parameters or not may be set. In this case, for example, the difference information may be acquired in one of the left and right subject eyes (for example, the left eye or the right eye) and whether to change the parameters of the left and right eyes may be set based on the difference result. It is needless to say that the above-described configuration is not limited to the difference information, and may be a comparison result.

In addition, in the present example, in each of the left eye and the right eye, it is set whether to change the parameters of the near distance objective eye refractive power and the far distance subjective eye refractive power, but the invention is not limited thereto. For example, in a case where the parameters of one of the left and right subject eyes are changed, the parameter of the other subject eye may also be changed. In other words, in a case of changing the parameters of one of the left and right subject eyes, the parameter may be automatically changed for the other one of the subject eyes. In addition, in the above-described case, the difference information may be acquired for each of the left and right eyes, or the difference information may be acquired only in one of the left and right eyes. It is needless to say that the above-described configuration is not limited to the difference information, and may be a comparison result.

In addition, in the present example, the difference information acquired for each of the left and right subject eyes (for example, the left eye and the right eye) may be comprehensively determined. In this case, for example, in a case where the difference information of one subject eye exceeds a predetermined threshold value with respect to the difference information on the left and right subject eyes, it may be set to perform the change of the parameters of both the left and right eyes. It is needless to say that the above-described configuration is not limited to the difference information, and may be a comparison result.

In addition, in the present example, a configuration for obtaining the difference value between the astigmatic power 202 in the near distance objective eye refractive power and the astigmatic power 203 in the far distance subjective eye refractive power as the difference information, has been described as an example, but the invention is not limited thereto. For example, the difference information may be a difference value between at least any parameter of the near distance objective eye refractive power and at least any parameter of the far distance subjective eye refractive power. For example, a configuration for obtaining a difference value between the astigmatic axis angle in the near distance objective eye refractive power and the astigmatic axis angle in the far distance subjective eye refractive power as the difference information, may be employed.

In addition, in the subjective optometry apparatus of the present disclosure, the examining step of the subjective examination may be changed based on the near distance objective eye refractive power. In this case, for example, the control portion may change the examining step performed in the subjective optometry apparatus based on the near distance objective eye refractive power. Accordingly, for example, it is possible to set the examining step in accordance with the near distance objective eye refractive power, to rapidly complete the subjective examination, and to acquire the subjective eye refractive power with higher accuracy. In particular, for example, in a case of performing the subjective examination of the near distance viewing state, it is possible to start the subjective examination in the near distance viewing state from the result of the near distance objective eye refractive power, and thus, it becomes possible to more rapidly obtain the measurement result than a case of starting the subjective examination of the near distance viewing state from the result of the far distance objective eye refractive power.

In addition, for example, as a change of the examining step, a configuration for setting whether to perform the far subjective examination and the near subjective examination for measuring the eye refractive power may be employed. In this case, for example, the acquisition portion may acquire the far distance objective eye refractive power obtained by objectively measuring the eye refractive power of the subject eye in the far distance viewing state together with the near distance objective eye refractive power. In addition, for example, the control portion may set to perform at least any subjective examination of the far subjective examination for subjectively measuring the eye refractive power of the subject eye in the far distance viewing state and the near subjective examination for subjectively measuring the eye refractive power of the subject eye in the near distance viewing state, based on the comparison result of the near distance objective eye refractive power and the far distance objective eye refractive power. Accordingly, for example, based on the comparison result, it is set as to which subjective examination is to be performed, and thus, only the subjective examination can be performed as necessary and the subjective examination can be rapidly performed. In addition, it is possible to suppress forgetting to perform the required subjective examination, and to acquire an appropriate subjective eye refractive power.

In addition, for example, as a change of the examining step, a configuration for setting priority of the far subjective examination and the near subjective examination for measuring the eye refractive power may be employed. In addition, for example, the control portion may set to preferentially perform the subjective examination among the far subjective examination for subjectively measuring the eye refractive power of the subject eye in the far distance viewing state and the near subjective examination for subjectively measuring the eye refractive power of the subject eye in the near distance viewing state, based on the comparison result. Accordingly, for example, by setting to preferentially perform any subjective examination of the far subjective examination and the near subjective examination, it becomes possible to perform the subjective examination in order in which the examination is likely to be rapidly completed, and to acquire the subjective eye refractive power with higher accuracy. As an example, for example, in a case of acquiring the near distance subjective eye refractive power, by preferentially performing the subjective examination in the near distance viewing state and by performing the examination focusing on the subjective examination in the near distance viewing state, it is possible to acquire the near distance subjective eye refractive power with higher accuracy, to proceed the examination with reference to the near distance subjective eye refractive power at the time of the subjective examination in the far distance viewing state, and thus, to rapidly complete the subjective examination.

1 subjective optometry apparatus
2 housing
3 presentation window
4 holding unit
5 connecting portion
6 moving unit
7 shaft
8 first operation portion
9 second operation portion
10 light projecting optical system
11 display
30 driving portion
31 base
32 block
35 holding arm
36 block receiver
38 supporting member
39 block receiver
40 observation unit
50 optometry unit
53 examination window
60 cornea position aiming optical system
80 control portion
85 supporting member
100 objective eye refractive power measurement apparatus

What is claimed is:

1. A subjective optometry apparatus for acquiring a subjective eye refractive power by subjectively measuring an eye refractive power of a subject eye, comprising:
    a light projecting optical system that has a visual target presenting portion for emitting a target light flux, and projects a target light flux emitted from the visual target presenting portion toward the subject eye;
    a calibration portion that is disposed in an optical path of the light projecting optical system, and changes optical characteristics of the target light flux;
    an acquisition portion configured to acquire a near distance objective eye refractive power that is an eye refractive power of the subject eye objectively measured in a near distance viewing state; and
    a control portion configured control an operation for acquiring a near distance subjective eye refractive power that is a subjective eye refractive power of the subject eye measured in a near distance viewing state, based on the near distance objective eye refractive power; and
    wherein the control portion sets the near distance objective eye refractive power as an initial value of the calibration portion when the control portion acquires the near distance subjective eye refractive power.

2. The subjective optometry apparatus according to claim 1,
    wherein the control portion sets at least near distance objective astigmatism information indicating the near distance objective eye refractive power as an initial value in the calibration portion when the control portion acquires the near distance subjective eye refractive power.

3. The subjective optometry apparatus according to claim 1,
    wherein in a case where the control portion acquires the near distance subjective eye refractive power based on a far distance subjective eye refractive power that is a subjective eye refractive power of the subject eye measured in a far distance viewing state, the control portion acquires the far distance subjective eye refractive power and sets an optical parameter of the far distance subjective eye refractive power to be changeable to a corresponding parameter in the near distance objective eye refractive power based on a comparison result of the near distance objective eye refractive power and the far distance subjective eye refractive power.

4. The subjective optometry apparatus according to claim 3,
    wherein the comparison result is a result of comparing at least far distance subjective astigmatism information of the far distance subjective eye refractive power with at least near distance objective astigmatism information of the near distance objective eye refractive power.

5. The subjective optometry apparatus according to claim 3,
    wherein the control portion acquires a difference information between the near distance objective eye refractive power and the far distance subjective eye refractive power as the comparison result, and sets the optical parameter of the far distance subjective eye refractive power to be changeable to a corresponding parameter in the near distance objective eye refractive power based on the difference information.

6. The subjective optometry apparatus according to claim 5, wherein the optical parameter comprises spherical power, astigmatic power, or astigmatic axis angle.

7. The subjective optometry apparatus according to claim 3, wherein the optical parameter comprises spherical power, astigmatic power, or astigmatic axis angle.

8. The subjective optometry apparatus according to claim 1, further comprising:
  a housing that accommodates the light projecting optical system; and
  a holding member that holds the calibration portion,
  wherein the holding member integrally connects the housing and the calibration portion.

9. A non-transitory computer readable recording medium storing a subjective optometry program used in a subjective optometry apparatus for acquiring a subjective eye refractive power by subjectively measuring an eye refractive power of a subject eye, including a light projecting optical system that has a visual target presenting portion for emitting a target light flux and projects a target light flux emitted from the visual target presenting portion toward the subject eye, and a calibration portion that is disposed in an optical path of the light projecting optical system and changes optical characteristics of the target light flux,
  wherein the subjective optometry program is executed by a processor of the subjective optometry apparatus to cause the subjective optometry apparatus to execute:
  a step of acquiring a near distance objective eye refractive power that is an eye refractive power of the subject eye objectively measured in a near distance viewing state; and
  a step of controlling an operation for acquiring a near distance subjective eye refractive power that is a subjective eye refractive power of the subject eye measured in a near distance viewing state, based on the near distance objective eye refractive power;
  wherein the step of controlling an operation sets the near distance objective eye refractive power as an initial value of the calibration portion when acquiring the near distance subjective eye refractive power.

* * * * *